United States Patent
Charrier et al.

(10) Patent No.: US 8,067,417 B2
(45) Date of Patent: Nov. 29, 2011

(54) IMIDAZO[1,2-F]PTERIDINES USEFUL AS INHIBITORS OF PROTEIN KINASES

(75) Inventors: Jean-Damien Charrier, Abingdon (GB); David Kay, Abingdon (GB); Ronald Knegtel, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/796,174

(22) Filed: Jun. 8, 2010

(65) Prior Publication Data

US 2011/0021519 A1    Jan. 27, 2011

Related U.S. Application Data

(62) Division of application No. 11/786,578, filed on Apr. 12, 2007, now Pat. No. 7,763,629.

(60) Provisional application No. 60/791,327, filed on Apr. 12, 2006, provisional application No. 60/838,720, filed on Aug. 18, 2006.

(51) Int. Cl.
*A61K 31/495*    (2006.01)

(52) U.S. Cl. .................................... 514/250; 544/252

(58) Field of Classification Search ............... 514/250; 544/252

See application file for complete search history.

(56) References Cited

FOREIGN PATENT DOCUMENTS

| | | |
|---|---|---|
| WO | WO97/44038 | 11/1997 |
| WO | WO00/12497 | 3/2000 |
| WO | WO02/076985 | 10/2002 |
| WO | WO2004/030635 | 4/2004 |
| WO | WO2004/108138 | 12/2004 |
| WO | WO2005/068466 | 7/2005 |
| WO | WO2005/121152 | 12/2005 |
| WO | WO2005/123736 | 12/2005 |

OTHER PUBLICATIONS

Jordan, V. C. Nature Reviews: Drug Discovery, 2, 2003, p. 205.
Dörwald, F. Zaragoza, Side Reactions in Organic Synthesis: A Guide to Successful Synthesis Design, Weinheim: WILEY-VCH Verlag GmbH & Co. KGaA, 2005, Preface.
International Preliminary Report on Patentability as issued by PCT on Oct. 14, 2008 with regard to PCT/US2007/009006.

*Primary Examiner* — James O Wilson
*Assistant Examiner* — Douglas M Willis
(74) *Attorney, Agent, or Firm* — Rory C. Stewart

(57) ABSTRACT

The present invention relates to compounds useful as inhibitors of protein kinase, represented by Structural Formula (I):

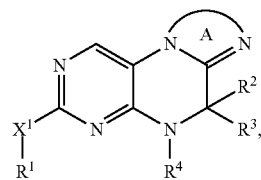

wherein the variables in Structural Formula (I) are as described herein. The invention also provides pharmaceutically acceptable compositions comprising said compounds and methods of using the compositions in the treatment of various disease, conditions, or disorders. The invention also provides processes for preparing compounds of the inventions.

27 Claims, No Drawings

US 8,067,417 B2

IMIDAZO[1,2-F]PTERIDINES USEFUL AS INHIBITORS OF PROTEIN KINASES

RELATED APPLICATIONS

This application is a divisional of U.S. Ser. No. 11/786,578 filed Apr. 12, 2007, which claims priority to U.S. Ser. No. 60/791,327, filed on Apr. 12, 2006 and U.S. Ser. No. 60/838,720, filed on Aug. 18, 2006. The entire teachings of these applications are incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g. protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g. shock, heat shock, ultraviolet radiation, bacterial endotoxin, and $H_2O_2$), cytokines (e.g. interleukin-1 (IL-1) and tumor necrosis factor alpha (TNF-a), and growth factors (e.g. granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (Plk) belong to a family of serine/threonine kinases that are highly conserved across the species, ranging from yeast to man (reviewed in Lowery D M et al., *Oncogene* 2005, 24;248-259). The Plk kinases have multiple roles in cell cycle, including control of entry into and progression through mitosis.

Plk1 is the best characterized of the Plk family members. Plk1 is widely expressed and is most abundant in tissues with a high mitotic index. Protein levels of Plk1 rise and peak in mitosis (Hamanaka, R et al., *J Biol Chem* 1995, 270, 21086-21091). The reported substrates of Plk1 are all molecules that are known to regulate entry and progression through mitosis, and include CDC25C, cyclin B, p53, APC, BRCA2 and the proteasome. Plk1 is upregulated in multiple cancer types and the expression levels correlate with severity of disease (Macmillan, J C et al., *Ann Surg Oncol* 2001, 8, 729-740). Plk1 is an oncogene and can transform NIH-3T3 cells (Smith, M R et al., *Biochem Biophys Res Commun* 1997, 234, 397-405). Depletion or inhibition of Plk1 by siRNA, antisense, microinjection of antibodies, or transfection of a dominant negative construct of Plk1 into cells, reduces proliferation and viability of tumour cells in vitro (Guan, R et al., *Cancer Res* 2005, 65, 2698-2704; Liu, X et al., Proc Natl Acad Sci USA 2003, 100, 5789-5794, Fan, Y et al., *World J Gastroenterol* 2005, 11, 4596-4599; Lane, H A et al., *J Cell Biol* 1996, 135, 1701-1713). Tumour cells that have been depleted of Plk1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of Plk1. In vivo knock down of Plk1 by siRNA or the use of dominant negative constructs leads to growth inhibition or regression of tumours in xenograft models.

Plk2 is mainly expressed during the G1 phase of the cell cycle and is localized to the centrosome in interphase cells. Plk2 knockout mice develop normally, are fertile and have normal survival rates, but are around 20% smaller than wild type mice. Cells from knockout animals progress through the cell cycle more slowly than in normal mice (Ma, S et al., *Mol Cell Biol* 2003, 23, 6936-6943). Depletion of Plk2 by siRNA or transfection of kinase inactive mutants into cells blocks centriole duplication. Downregulation of Plk2 also sensitizes tumour cells to taxol and promotes mitotic catastrophe, in part by suppression of the p53 response (Burns T F et al., *Mol Cell Biol* 2003, 23, 5556-5571).

Plk3 is expressed throughout the cell cycle and increases from G1 to mitosis. Expression is upregulated in highly proliferating ovarian tumours and breast cancer and is associated with a worse prognosis (Weichert, W et al., *Br J Cancer* 2004, 90, 815-821; Weichert, W et al., *Virchows Arch* 2005, 446, 442-450). In addition to regulation of mitosis, Plk3 is believed to be involved in Golgi fragmentation during the cell cycle and in the DNA-damage response Inhibition of Plk3 by dominant negative expression is reported to promote p53-independent apoptosis after DNA damage and suppresses colony formation by tumour cells (Li, Z et al., *J Biol Chem* 2005, 280, 16843-16850.

Plk4 is structurally more diverse from the other Plk family members. Depletion of this kinase causes apoptosis in cancer cells (Li, J et al., *Neoplasia* 2005, 7, 312-323). Plk4 knockout mice arrest at E7.5 with a high fraction of cells in mitosis and partly segregated chromosomes (Hudson, J W et al., *Current Biology* 2001, 11, 441-446).

Molecules of the protein kinase family have been implicated in tumour cell growth, proliferation and survival. Accordingly, there is a great need to develop compounds useful as inhibitors of protein kinases. The evidence implicating the Plk kinases as essential for cell division is strong. Blockade of the cell cycle is a clinically validated approach to inhibiting tumour cell proliferation and viability. It would therefore be desirable to develop compounds that are useful as inhibitors of the Plk family of protein kinases (e.g. Plk1, Plk2, Plk3 and Plk4), that would inhibit proliferation and reduce viability of tumour cells, particularly as there is a strong medical need to develop new treatments for cancer.

SUMMARY OF THE INVENTION

This invention relates to compounds of formula I

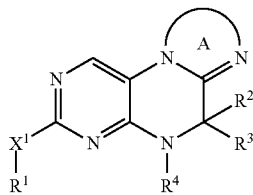

I wherein:

Ring A is a 5-membered heteroaryl ring wherein the ring is optionally substituted with $C_{1-6}$ haloalkyl, halo, $NO_2$, —OH, —CN or an optionally substituted $C_{1-6}$ alkyl;

$X^1$ is a bond, —O—, —$NR^8$—, —S—, —S(O)—, or —$S(O)_2$—;

$R^1$ is H, $C_{1-10}$ aliphatic, $C_{3-10}$ cycloaliphatic, $C_{6-10}$ aryl, 5-10 membered heteroaryl, or 3-10 membered heterocyclyl, wherein said $R^1$ is optionally substituted with 0-5 $J^1$;

Each $R^2$ and $R^3$ is independently H, $C_{1-10}$ aliphatic, or $C_{3-10}$ cycloaliphatic, wherein each $R^2$ and $R^3$ is optionally and independently substituted with 0-5 $J^2$ and $J^3$ respectively, or $R^2$ and $R^3$, together with the carbon atom to which they are attached, form a 3-8 membered saturated or partially unsaturated monocyclic ring containing 0-4 heteroatoms independently selected from O, N, and S, wherein said monocyclic ring formed by $R^2$ and $R^3$ is optionally substituted with 0-4 $J^{23}$;

$R^4$ is H, —C(O)R, —C(O)OR, —C(O)NRR', $C_{1-10}$ aliphatic, $C_{3-10}$ cycloaliphatic, $C_{6-10}$ aryl, $C_{5-10}$ heteroaryl, 3-10 membered heterocyclyl, ($C_{1-6}$ aliphatic)-($C_{3-10}$ cycloaliphatic), ($C_{1-6}$ aliphatic)-($C_{6-10}$ aryl), or ($C_{1-6}$ aliphatic)-(5-10 membered heteroaryl), wherein said $R^4$ is optionally substituted with 0-5 $J^4$;

$R^8$ is H, $C_{1-6}$ aliphatic, $C_{3-8}$ cycloaliphatic, —C(O)R, —C(O)OR, or —C(O)NRR';

Each $J^1$ is independently $C_{1-6}$haloalkyl, halo, $NO_2$, CN, Q, or -Z-Q, or two $J^1$ taken together can optionally form =O;

Each Z is independently $C_{1-6}$ aliphatic in which 0-3 —$CH_2$— units in said $C_{1-6}$ aliphatic are optionally replaced with —NR—, —O—, —S—, —C(O)—, —C(=NR)—, —C(=NOR)—, —S(O)—, or —$S(O)_2$—, wherein any non-replaced —$CH_2$— units in said $C_{1-6}$ aliphatic are optionally substituted with 0-2 $J^z$;

Each Q is independently H, $C_{1-6}$ aliphatic, a 3-8-membered aromatic or non-aromatic monocyclic ring having 0-3 heteroatoms independently selected from O, N, and S, or an 8-12 membered aromatic or non-aromatic bicyclic ring system having 0-5 heteroatoms independently selected from O, N, and S, wherein each Q is optionally substituted with 0-5 $J^Q$;

Each $J^2$ and $J^3$ is independently $C_{1-6}$ aliphatic, $C_{3-6}$ cycloaliphatic, or —$(C_{1-4}alkyl)_n$—$V^1$, wherein n is 0 or 1, each $V^1$ is independently halo($C_{1-4}$ aliphatic), —O(halo$C_{1-4}$ aliphatic), halo, $NO_2$, CN, OH, OR"SH, SR", $NH_2$, NHR", $N(R")_2$, COH, COR", $CO_2H$, $CO_2R"$, $CONH_2$, CONHR", CONR"$_2$, OCOR", $OCONH_2$, OCONHR", OCON(R")$_2$, NHCOR", NR"COR", $NHCO_2R"$, $NR"CO_2R"$, $NHCO_2H$, $NR"CO_2H$, $NHCONH_2$, NHCONHR", NHCON(R")$_2$, $SO_2NH_2$, $SO_2NHR"$, $SO_2N(R")_2$, $NHSO_2R"$, $NR"SO_2R"$, or $V^1$ is a cyclic group selected from $C_{3-6}$ cycloaliphatic, phenyl, 5-6 membered heteroaryl, or 3-6 membered heterocyclyl, wherein said cyclic group is optionally substituted with 0-3 $J^V$;

Each R" is independently unsubstituted $C_{1-4}$ aliphatic, or two of the same $J^2$ and $J^3$ bonded to the same atom, together can optionally form =O;

Each $J^Z$ and $J^V$ is independently halo, $C_{1-6}$ aliphatic, $C_{3-6}$ cycloaliphatic, $NO_2$, CN, OH, $NH_2$, NH($C_{1-4}$ aliphatic), N($C_{1-4}$ aliphatic)$_2$, —O($C_{1-4}$ aliphatic), —$CO_2H$, —$CO_2$($C_{1-4}$ aliphatic), —O(halo$C_{1-4}$ aliphatic), or halo($C_{1-4}$ aliphatic);

Each $J^Q$, $J^4$, and $J^{23}$ is independently -M or -Y-M;

Each Y is independently an unsubstituted $C_{1-6}$ aliphatic in which 0-3 —$CH_2$— units in said $C_{1-6}$ aliphatic are optionally replaced with —NR—, —O—, —S—, —C(O)—, —S(O)—, or —$S(O)_2$—;

Each M is independently H, $C_{1-6}$ aliphatic, $C_{3-6}$ cycloaliphatic, halo($C_{1-4}$ aliphatic), O(halo$C_{1-4}$ aliphatic), 3-6 membered heterocyclyl, halo, $NO_2$, CN, OH, OR', SH, SR', $NH_2$, NHR', $N(R')_2$, COH, COR', $CO_2H$, $CO_2R'$, $CONH_2$, CONHR', CONR'$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, or $NR'SO_2R'$;

Each R is independently H or unsubstituted $C_{1-6}$ aliphatic; and

Each R' is unsubstituted $C_{1-6}$ aliphatic, or two R' groups, together with the atom to which they are bound, form an unsubstituted 3-8 membered saturated or partially unsaturated monocyclic ring having 0-1 heteroatoms independently selected from O, N, and S.

Compounds of this invention, and pharmaceutically acceptable compositions thereof, are effective as inhibitors of protein kinases. In some embodiments, these compounds are effective as inhibitors of PLK protein kinases; in some embodiments, as inhibitors of PLK1 protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease, a neurodegenerative disease, or an immunologically-mediated disease. The compounds provided by this invention are also useful for the study of kinases in biological and pathological phenomena; the study of intracellular signal transduction pathways mediated by such kinases; and the comparative evaluation of new kinase inhibitors.

Compounds of this invention include those described herein, and are further illustrated by the classes, subclasses, and species disclosed herein (see e.g. Embodiments 1-22). As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic C3-C8 hydrocarbon or bicyclic C8-C12 hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopentenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "nonaromatic", as used herein, describes rings that are either saturated or partially unsaturated.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally replaced with another atom or group. This means that a methylene unit of the alkyl or aliphatic chain is optionally replaced with said other atom or group. Examples of such atoms or groups would include, but are not limited to, —NR—, —O—, —C(O)—, —C(=N—CN)—, —C(=NR)—, —C(=NOR)—, —S—, —SO—, or —SO$_2$—. These atoms or groups can be combined to form larger groups. Examples of such groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is defined herein.

Unless otherwise specified, the optional replacements form a chemically stable compound. Optional replacements can occur both within the chain and at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise specified, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise stated, structures depicted herein are also meant to include all isomeric (e.g., enantiomeric, diastereomeric, geometric, conformational, and rotational forms of the structure). For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

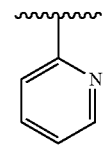

also represents

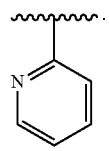

Therefore, single stereochemical isomers as well as enantiomeric, diastereomeric, geometric, conformational, or rotational mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention can exist in free form for treatment, or where appropriate, as a pharmaceutically acceptable salt.

As used herein, the term "pharmaceutically acceptable salt" refers to salts of a compound which are suitable for the intended use. In some embodiments, the salts are suitable for use in contact with the tissues of humans and lower animals without undue toxicity, irritation, allergic response and the like, and are commensurate with a reasonable benefit/risk ratio. In other embodiments, the salts may be suitable for use in in vitro assays, kinetic studies, crystallographic studies and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:
LG leaving group
TBTU O-(Benzotriazol-1-yl)-N,N,N',N'-tetramethyluronium tetrafluoroborate
DMSO dimethyl sulfoxide
DMA dimethyl acetamide
TCA trichloroacetic acid
ATP adenosine triphosphate
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time

DETAILED DESCRIPTION OF THE INVENTION

In some aspects, the invention provides compounds of formula I or a pharmaceutically acceptable salt useful as inhibitors of protein kinases

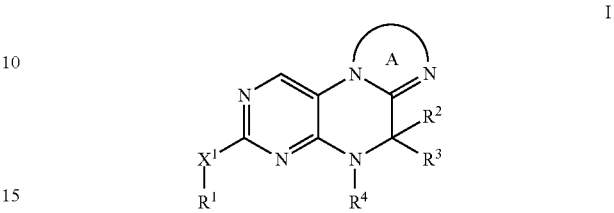

wherein:
Ring A is a 5-membered heteroaryl ring wherein the ring is optionally substituted with $C_{1-6}$ haloalkyl, halo, $NO_2$, —OH, —CN or an optionally substituted $C_{1-6}$ alkyl;
$X^1$ is a bond, —O—, —$NR^8$—, —S—, —S(O)—, or —S(O)$_2$—;
$R^1$ is H, $C_{1-10}$ aliphatic, $C_{3-10}$ cycloaliphatic, $C_{6-10}$ aryl, 5-10 membered heteroaryl, or 3-10 membered heterocyclyl, wherein said $R^1$ is optionally substituted with 0-5 $J^1$;
Each $R^2$ and $R^3$ is independently H, $C_{1-10}$aliphatic, or $C_{3-10}$ cycloaliphatic, wherein each $R^2$ and $R^3$ is optionally and independently substituted with 0-5 $J^2$ and $J^3$ respectively, or
$R^2$ and $R^3$, together with the carbon atom to which they are attached, form a 3-8 membered saturated or partially unsaturated monocyclic ring containing 0-4 heteroatoms independently selected from O, N, and S, wherein said monocyclic ring formed by $R^2$ and $R^3$ is optionally substituted with 0-4 $J^{23}$;
$R^4$ is H, —C(O)R, —C(O)OR, —C(O)NRR', $C_{1-10}$aliphatic, $C_{3-10}$ cycloaliphatic, $C_{6-10}$ aryl, $C_{5-10}$ heteroaryl, 3-10 membered heterocyclyl, ($C_{1-6}$ aliphatic)-($C_{3-10}$ cycloaliphatic), ($C_{1-6}$ aliphatic)-($C_{6-10}$ aryl), or ($C_{1-6}$ aliphatic)-(5-10 membered heteroaryl), wherein said $R^4$ is optionally substituted with 0-5 $J^4$;
$R^8$ is H, $C_{1-6}$ aliphatic, $C_{3-8}$ cycloaliphatic, —C(O)R, —C(O)OR, or —C(O)NRR';
Each $J^1$ is independently $C_{1-6}$ haloalkyl, halo, $NO_2$, CN, Q, or -Z-Q, or two $J^1$ taken together can optionally form =O;
Each Z is independently $C_{1-6}$ aliphatic in which 0-3 —$CH_2$— units in said $C_{1-6}$ aliphatic are optionally replaced with —NR—, —O—, —S—, —C(O)—, —C(=NR)—, —C(=NOR)—, —S(O)—, or —S(O)$_2$—, wherein any non-replaced —$CH_2$— units in said $C_{1-6}$ aliphatic are optionally substituted with 0-2 $J^Z$;
Each Q is independently H, $C_{1-6}$ aliphatic, a 3-8-membered aromatic or non-aromatic monocyclic ring having 0-3 heteroatoms independently selected from O, N, and S, or an 8-12 membered aromatic or non-aromatic bicyclic ring system having 0-5 heteroatoms independently selected from O, N, and S, wherein each Q is optionally substituted with 0-5 $J^Q$;
Each $J^2$ and $J^3$ is independently $C_{1-6}$ aliphatic, $C_{3-6}$ cycloaliphatic, or —($C_{1-4}$alkyl)$_n$—$V^1$, wherein
n is 0 or 1,
each $V^1$ is independently halo($C_{1-4}$ aliphatic), —O(halo$C_{1-4}$ aliphatic), halo, $NO_2$, CN, OH, OR", SH, SR", $NH_2$, NHR", N(R")$_2$, COH, COR", $CO_2H$, $CO_2R$", $CONH_2$, CONHR", CONR"$_2$, OCOR", OCONH$_2$, OCONHR", OCON(R")$_2$, NHCOR", NR"COR", NHCO$_2$R", NR"CO$_2$R", NHCO$_2$H, NR"CO$_2$H, NHCONH$_2$, NHCONHR", NHCON(R")$_2$, SO$_2$NH$_2$, SO$_2$NHR", SO$_2$N(R")$_2$, NHSO$_2$R", NR"SO$_2$R", or V$^1$ is a cyclic group selected from C$_{3-6}$ cycloaliphatic, phenyl, 5-6 membered heteroaryl, or 3-6 membered heterocyclyl, wherein said cyclic group is optionally substituted with 0-3 J$^V$;

Each R" is independently unsubstituted C$_{1-4}$ aliphatic, or two of the same J$^2$ and J$^3$ bonded to the same atom, together can optionally form =O;

Each J$^Z$ and J$^V$ is independently halo, C$_{1-6}$ aliphatic, C$_{3-6}$ cycloaliphatic, NO$_2$, CN, OH, NH$_2$, NH(C$_{1-4}$ aliphatic), N(C$_{1-4}$ aliphatic)$_2$, —O(C$_{1-4}$ aliphatic), —CO$_2$H, —CO$_2$(C$_{1-4}$ aliphatic), —O(haloC$_{1-4}$ aliphatic), or halo(C$_{1-4}$ aliphatic);

Each J$^Q$, J$^4$, and J$^{23}$ is independently -M or -Y-M;

Each Y is independently an unsubstituted C$_{1-6}$ aliphatic in which 0-3 —CH$_2$— units in said C$_{1-6}$ aliphatic are optionally replaced with —NR—, —O—, —S—, —C(O)—, —S(O)—, or —S(O)$_2$—;

Each M is independently H, C$_{1-6}$ aliphatic, C$_{3-6}$ cycloaliphatic, halo(C$_{1-4}$ aliphatic), O(haloC$_{1-4}$ aliphatic), 3-6 membered heterocyclyl, halo, NO$_2$, CN, OH, OR', SH, SR', NH$_2$, NHR', N(R')$_2$, COH, COR', CO$_2$H, CO$_2$R', CONH$_2$, CONHR', CONR'$_2$, OCOR', OCONH$_2$, OCONHR', OCON(R')$_2$, NHCOR', NR'COR', NHCO$_2$R', NR'CO$_2$R', NHCO$_2$H, NR'CO$_2$H, NHCONH$_2$, NHCONHR', NHCON(R')$_2$, SO$_2$NH$_2$, SO$_2$NHR', SO$_2$N(R')$_2$, NHSO$_2$R', or NR'SO$_2$R';

Each R is independently H or unsubstituted C$_{1-6}$ aliphatic; and

Each R' is unsubstituted C$_{1-6}$ aliphatic, or two R' groups, together with the atom to which they are bound, form an unsubstituted 3-8 membered saturated or partially unsaturated monocyclic ring having 0-1 heteroatoms independently selected from O, N, and S.

In some embodiments, Ring A is a triazole ring optionally substituted with C$_{1-6}$ haloalkyl, halo, NO$_2$, OH, CN or optionally substituted C$_{1-6}$ alkyl.

In certain embodiments, Ring A is an imidazole ring optionally substituted with C$_{1-6}$ haloalkyl, halo, NO$_2$, OH, CN or optionally substituted C$_{1-6}$ alkyl.

In some embodiments, X$^1$ is —O—, —NR$^8$—, or —S—.

In other embodiments, X$^1$ is —NR$^8$—.

In some embodiments, R$^8$ is H or —C(O)OR wherein R is C$_{1-6}$ alkyl; for instance R$^8$ is —C(O)OCH$_3$.

In certain embodiments, R$^1$ is H, optionally substituted C$_{6-10}$ aryl, optionally substituted aralkyl or optionally substituted C$_{5-10}$ heteroaryl.

In some embodiments, R$^1$ is optionally substituted with —O-Q, halo, —C(O)N(R)-Q, or Q, in which each Q in Q, —C(O)N(R)-Q and —O-Q is independently optionally substituted with 0-5 J$^Q$.

In some embodiments, R$^1$ is phenyl optionally substituted at the para position with —C(O)N(R)-Q and any remaining position with —O-Q, halo, or Q, in which each Q in Q, —C(O)N(R)-Q and —O-Q is independently optionally substituted with 0-5 J$^Q$.

In some embodiments, J$^Q$ is a C$_{1-6}$ aliphatic optionally substituted with C$_{3-6}$ cycloaliphatic, halo(C$_{1-4}$ aliphatic), O(haloC$_{1-4}$ aliphatic), or 3-6 membered heterocyclyl.

In some embodiments, R$^1$ is heteroaryl is substituted with —C(O)N(R)-Q and any remaining position with —O-Q, or Q, in which each Q in Q, —C(O)N(R)-Q and —O-Q is independently optionally substituted with 0-5 J$^Q$.

In some embodiments, Q in —C(O)N(R)-Q is H, C$_{1-4}$ aliphatic, C$_{1-4}$ haloaliphatic, C$_{3-7}$ cycloaliphatic, C$_{3-7}$ heterocycloaliphatic, C$_{1-6}$ alkoxy, (C$_{1-6}$ alkoxy)C$_{1-6}$ alkyl or C$_{1-6}$ haloalkoxy.

In some embodiments, wherein R$^1$ is phenyl substituted with Q in the para position, the phenyl is optionally substituted at any remaining position with halo, C$_{1-4}$ aliphatic, C$_{1-4}$ haloaliphatic, C$_{3-7}$ cycloaliphatic, C$_{3-7}$ heterocycloaliphatic, C$_{1-6}$ alkoxy, (C$_{1-6}$ alkoxy)C$_{1-6}$ alkyl or C$_{1-6}$ haloalkoxy.

In some embodiments, Q of —C(O)N(R)-Q is methyl, ethyl, 1-methylpiperidin-4-yl, cyclopropyl, cyclopentyl, 3-furanyl, 3-fluoropyrrolidin-1-yl or 3,3-difluorocyclobutyl.

In some embodiments, R$^1$ is optionally substituted C$_{1-6}$ alkyl or C$_{3-7}$ cycloalkyl.

In certain embodiments, R$^1$ is phenyl substituted with at least one Q at the para position of the phenyl and Q is fluoro, carboxy, trifluoromethyl, 4-methylpiperazin-1-yl, difluoromethoxy, morpholin-1-yl, pyrazol-1-yl or pyrrolidin-1-yl.

In some instances, R$^1$ is a heteroaryl which is substituted with —C(O)N(R)-Q and at any remaining position with —O-Q, or Q, in which each Q in Q, —C(O)N(R)-Q and —O-Q is independently optionally substituted with 0-5 J$^Q$.

In some embodiments, Q in —C(O)N(R)-Q is H, C$_{1-4}$ aliphatic, C$_{1-4}$ haloaliphatic, C$_{3-7}$ cycloaliphatic, C$_{3-7}$ heterocycloaliphatic, C$_{1-6}$ alkoxy, (C$_{1-6}$ alkoxy)C$_{1-6}$ alkyl or C$_{1-6}$ haloalkoxy.

In still further embodiments, Q in —C(O)N(R)-Q is methyl, ethyl, 1-methylpiperidin-4-yl, cyclopropyl, cyclopentyl, 3-furanyl, 3-fluoropyrrolidin-1-yl or 3,3-difluorocyclobutyl.

In some instances, R$^1$ is optionally substituted C$_{1-6}$ alkyl or C$_{3-7}$ cycloalkyl. In still further instances, R$^1$ is H, ethyl, cyclopropyl or cyclopentyl.

In some embodiments, R$^1$ is phenyl substituted at the para position with Q or —ZQ. In some instances, the substituent at the para position is fluoro, carboxy, trifluoromethyl, 4-methylpiperazin-1-yl, difluoromethoxy, morpholin-1-yl, pyrazol-1-yl or pyrrolidin-1-yl.

In some embodiments, R$^1$ is thiophene-2-yl, pyridin-3-yl, pyridin-4-yl, or 6-trifluoromethylpyridin-3-yl.

In certain embodiments, each of R$^2$ and R$^3$ is independently H or a C$_{1-3}$ alkyl optionally and independently substituted with 0-5 J$^2$ and J$^3$. In some instances, R$^2$ is H and R$^3$ is C$_{1-3}$ alkyl, such as ethyl.

In other embodiments, R$^2$ and R$^3$, together with the carbon atom to which they are attached, form a 3-8 membered saturated or partially unsaturated monocyclic ring containing 0-4 heteroatoms independently selected from O, N, and S, wherein said monocyclic ring formed by R$^2$ and R$^3$ is optionally substituted with 0-4 J$^{23}$.

In some instances, J$^{23}$ is H, halo, C$_{1-4}$ alkyl, OH, C$_{1-4}$alkoxy, C$_{1-4}$haloalkoxy or amino.

In certain embodiments, each J$^2$ and J$^3$ is independently C$_{1-6}$ aliphatic, C$_{3-6}$ cycloaliphatic, or —(C$_{1-4}$alkyl)$_n$—V$^1$, wherein n is 0 or 1, each V$^1$ is independently halo(C$_{1-4}$ aliphatic), —O(haloC$_{1-4}$ aliphatic), halo, NO$_2$, CN, OH, OR", SH, SR", NH$_2$, NHR", N(R")$_2$, COH, COR", CO$_2$H, CO$_2$R", CONH$_2$, CONHR", CONR"$_2$, OCOR", OCONH$_2$, OCONHR", OCON(R")$_2$, NHCOR", NR"COR", NHCO$_2$R", NR"CO$_2$R", NHCO$_2$H, NR"CO$_2$H, NHCONH$_2$, NHCONHR", NHCON(R")$_2$, SO$_2$NH$_2$, SO$_2$NHR", SO$_2$N(R")$_2$, NHSO$_2$R", NR"SO$_2$R", or $V^1$ is a cyclic group selected from $C_{3-6}$ cycloaliphatic, phenyl, 5-6 membered heteroaryl, or 3-6 membered heterocyclyl, wherein said cyclic group is optionally substituted with 0-3 $J^V$; and each R" is independently unsubstituted $C_{1-4}$ aliphatic, or two of the same $J^2$ and $J^3$ bonded to the same atom, together can optionally form =O.

In some instances, each $J^2$ and $J^3$ is independently $C_{1-6}$ aliphatic, $C_{3-6}$ cycloaliphatic, or —$(C_{1-4}$alkyl$)_n$—$V^1$, wherein n is 0 or 1, each $V^1$ is independently halo($C_{1-4}$ aliphatic), —O(halo$C_{1-4}$ aliphatic), halo, $NO_2$, CN, OH, SH, $NH_2$, COH, $CO_2H$, $CONH_2$, $OCONH_2$, $NHCO_2H$, $NHCONH_2$, $SO_2NH_2$, or $V^1$ is a cyclic group selected from $C_{3-6}$ cycloaliphatic, phenyl, 5-6 membered heteroaryl, or 3-6 membered heterocyclyl, wherein said cyclic group is optionally substituted with 0-3 $J^V$; and each R" is independently unsubstituted $C_{1-4}$ aliphatic, or two of the same $J^2$ and $J^3$ bonded to the same atom, together can optionally form =O.

In other embodiments, each $J^2$ or $J^3$ is independently amino, amido, CN, OH, $C_{1-4}$ alkoxy, or $C_{1-4}$haloalkoxy and $V^1$ is H, halo, $C_{1-4}$ alkyl, OH, $C_{1-4}$alkoxy, $C_{1-4}$haloalkoxy or amino.

In some embodiments, $R^4$ is $C_{1-6}$ aliphatic, $C_{3-10}$ cycloaliphatic, $C_{3-10}$ heterocycloaliphatic, $C_{6-14}$ aryl or $C_{5-14}$ heteroaryl each optionally substituted with 0-5 $J^4$.

In some embodiments, $R^4$ is cyclopentyl.

In some embodiments, each $J^Q$, $J^4$, and $J^{23}$ is independently -M or -Y-M.

In certain embodiments, each Y is independently an unsubstituted $C_{1-6}$ aliphatic in which 0-3 —$CH_2$— units in said $C_{1-6}$ aliphatic are optionally replaced with —NR—, —O—, —S—, —C(O)—, —S(O)—, or —$S(O)_2$—;

In other embodiments, each M is independently H, $C_{1-6}$ aliphatic, $C_{3-6}$ cycloaliphatic, halo($C_{1-4}$ aliphatic), O(halo$C_{1-4}$ aliphatic), 3-6 membered heterocyclyl, halo, $NO_2$, CN, OH, OR', SH, SR', $NH_2$, NHR', $N(R')_2$, COH, COR', $CO_2H$, $CO_2R'$, $CONH_2$, CONHR', $CONR'_2$, OCOR', $OCONH_2$, OCONHR', $OCON(R')_2$, NHCOR', NR'COR', $NHCO_2R'$, $NR'CO_2R'$, $NHCO_2H$, $NR'CO_2H$, $NHCONH_2$, NHCONHR', $NHCON(R')_2$, $SO_2NH_2$, $SO_2NHR'$, $SO_2N(R')_2$, $NHSO_2R'$, or $NR'SO_2R'$.

In other instances, each M is independently H, $C_{1-6}$ aliphatic, $C_{3-6}$ cycloaliphatic, halo($C_{1-4}$ aliphatic), O(halo$C_{1-4}$ aliphatic), 3-6 membered heterocyclyl, In some embodiments, compounds of the invention may be represented by formula II;

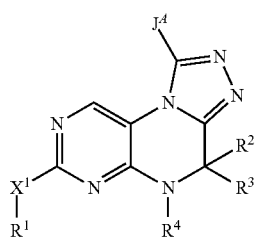

II wherein $X^1$, $R^1$, $R^2$, $R^3$ and $R^4$ are as previously described and $J^4$ is H, $C_{1-4}$ alkyl, or OH.

In some embodiments, the compounds of this invention are represented in Table 1.

TABLE 1

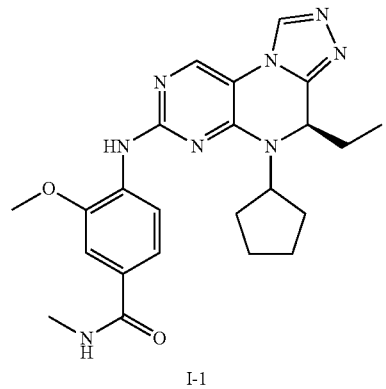

I-1

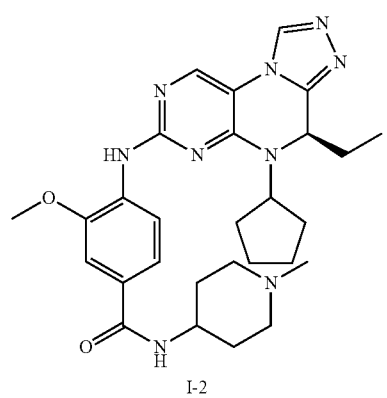

I-2

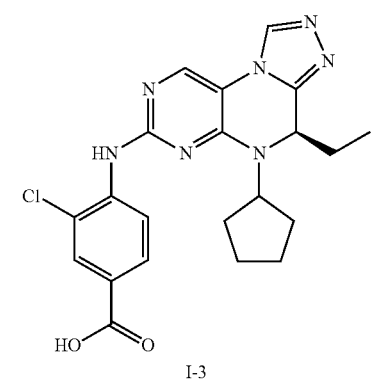

I-3

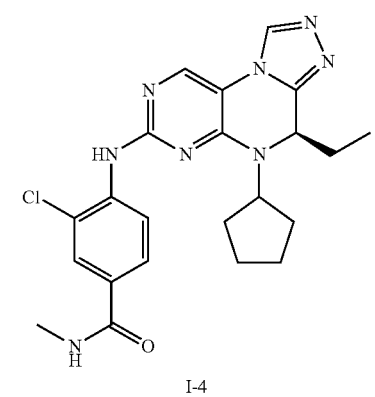

I-4

TABLE 1-continued
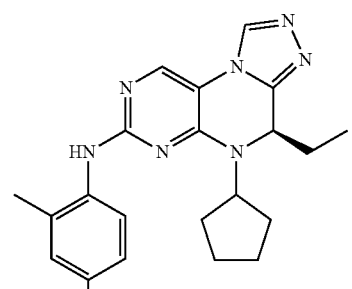
I-5
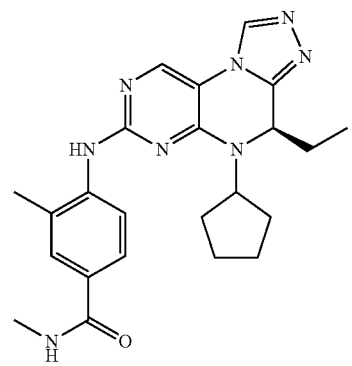
I-6
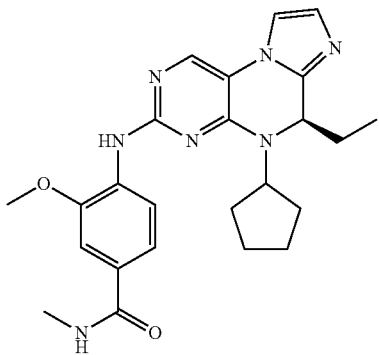
I-7
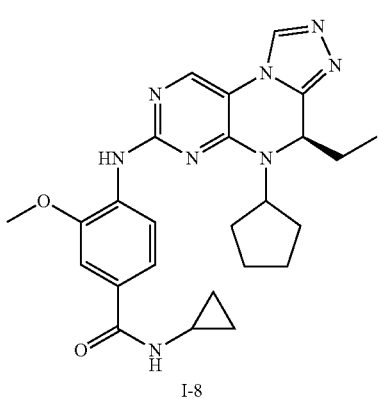
I-8
TABLE 1-continued
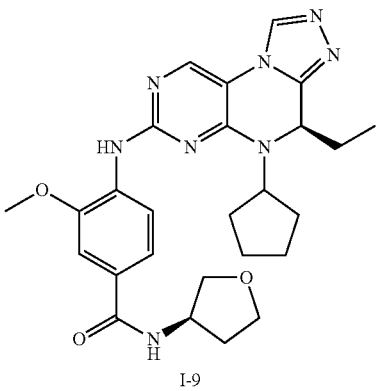
I-9
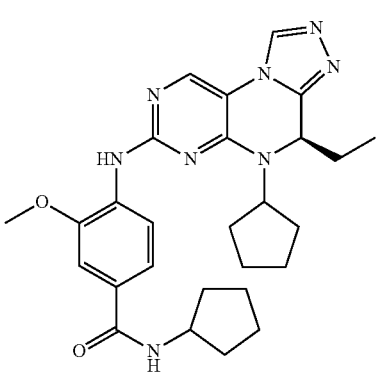
I-10
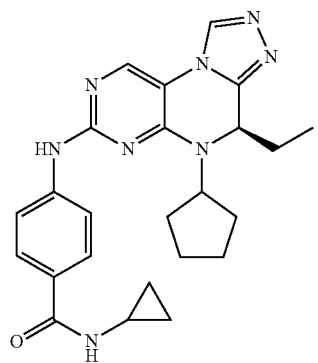
I-11
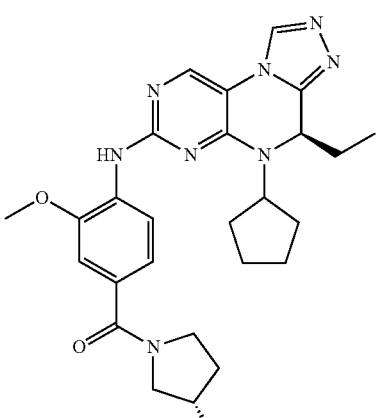
I-12

TABLE 1-continued
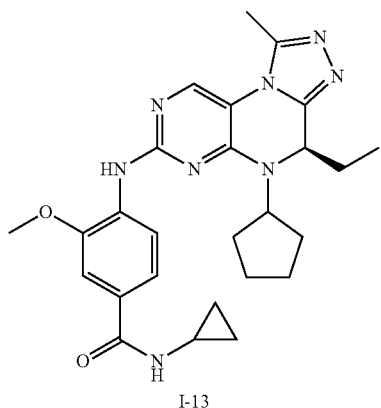
I-13
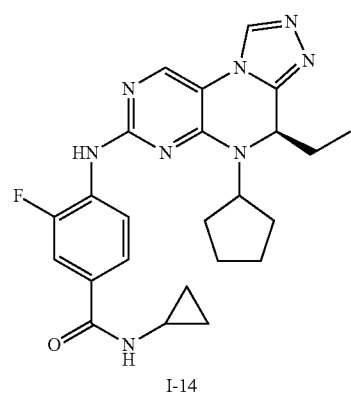
I-14
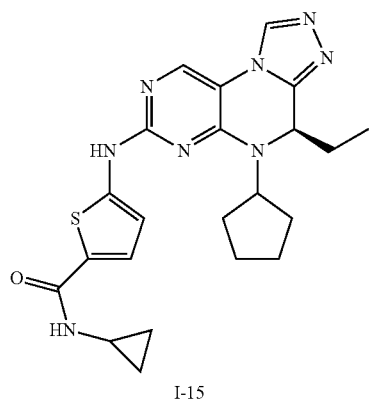
I-15
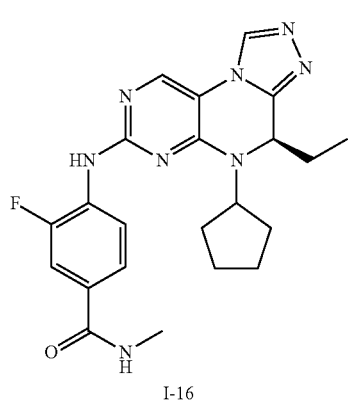
I-16
TABLE 1-continued
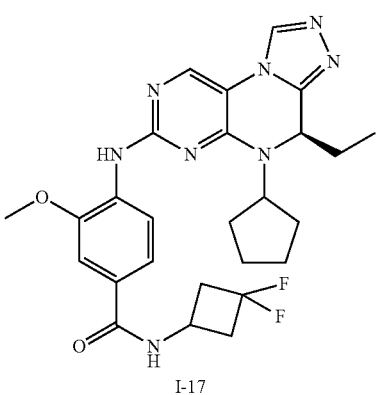
I-17
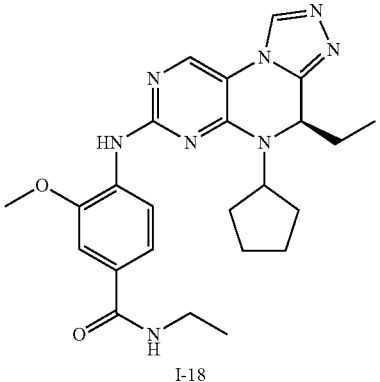
I-18
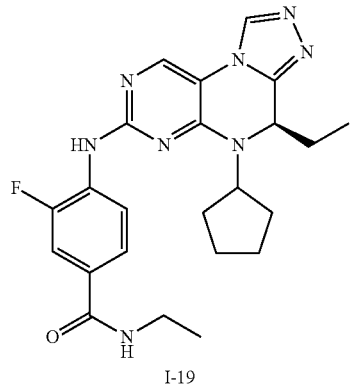
I-19
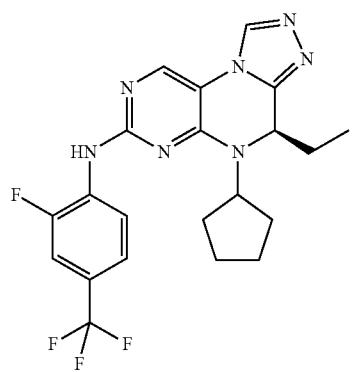
I-20

TABLE 1-continued
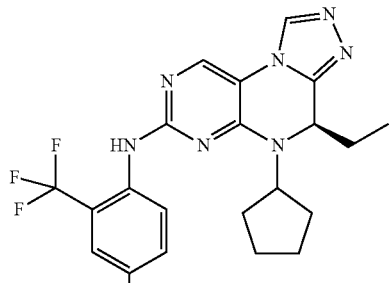
I-21
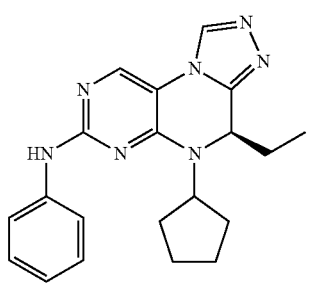
I-22
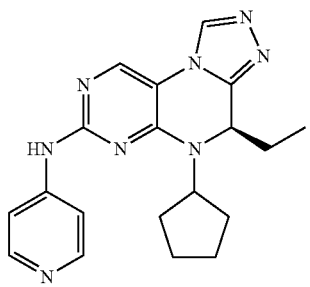
I-23
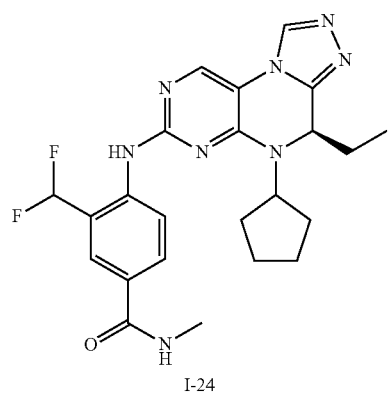
I-24
TABLE 1-continued
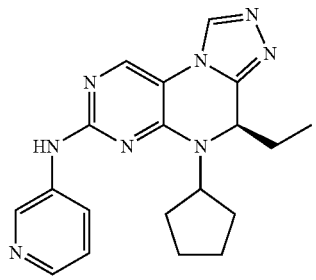
I-25
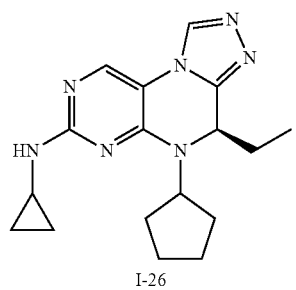
I-26
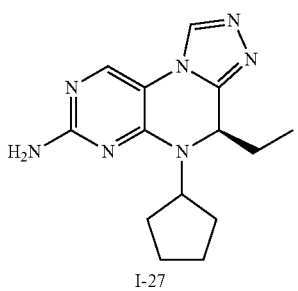
I-27
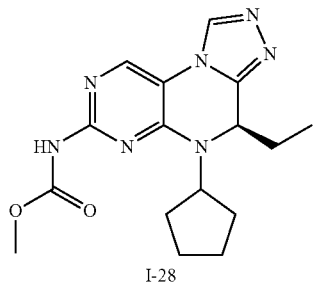
I-28
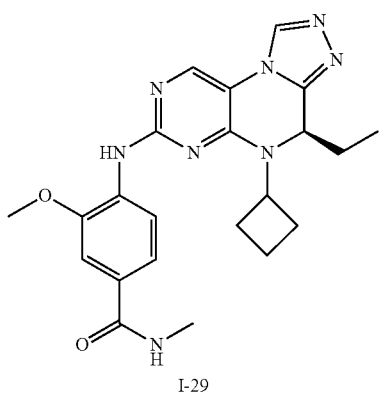
I-29

TABLE 1-continued
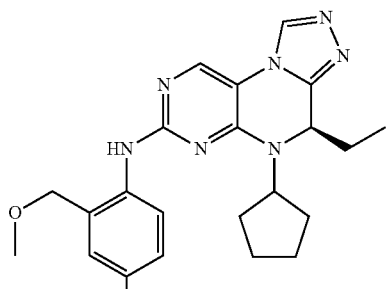
I-30
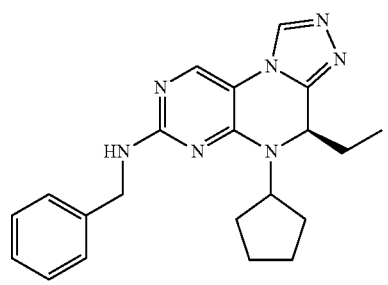
I-31
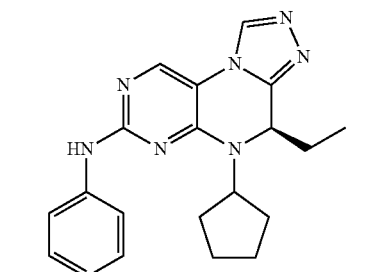
I-32
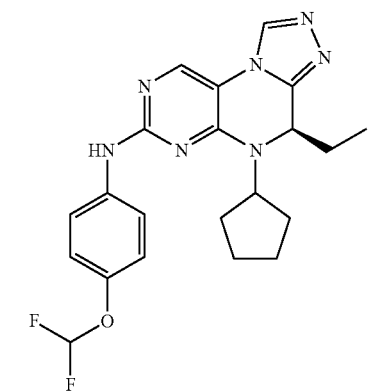
I-33
TABLE 1-continued
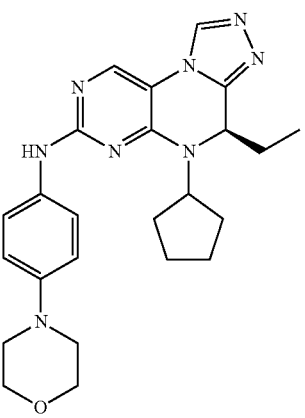
I-34
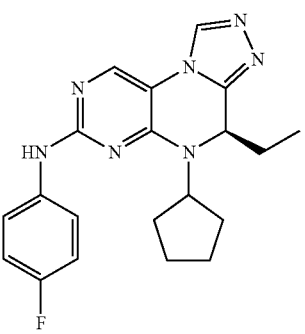
I-35
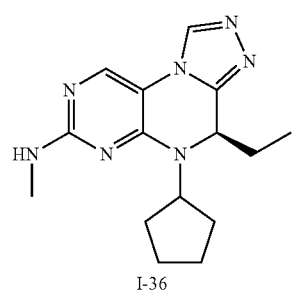
I-36
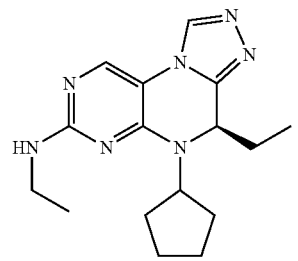
I-37

TABLE 1-continued

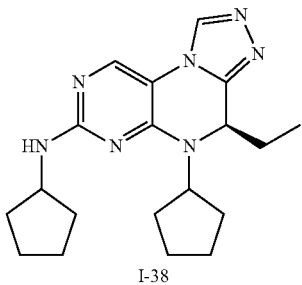

I-38

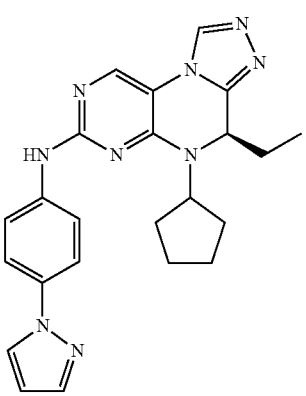

I-39

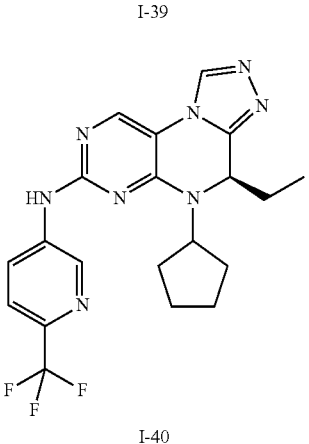

I-40

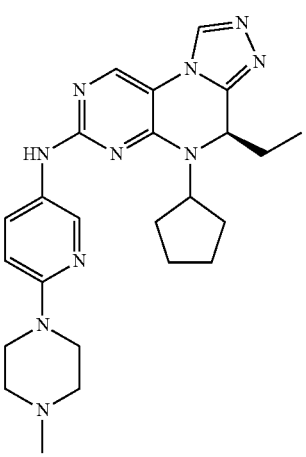

I-41

TABLE 1-continued

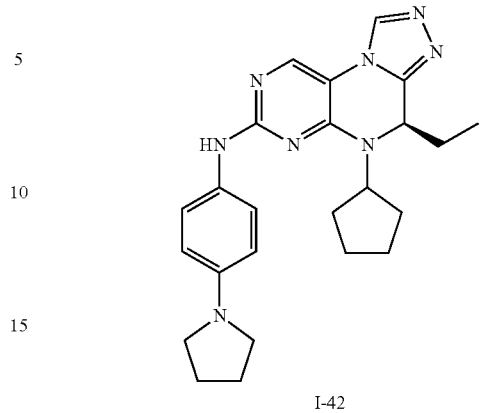

I-42

General Synthetic Methodology

The compounds of this invention may be prepared in general by methods such as those depicted in the general schemes below and the preparative examples that follow. Unless otherwise indicated, all variables in the following schemes are as defined herein.

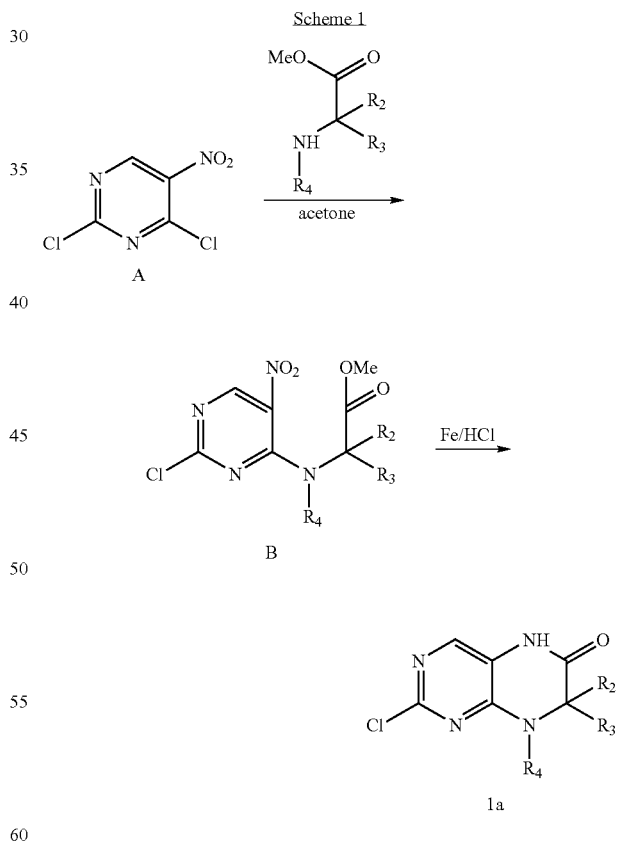

Scheme 1 above shows the synthetic route to give starting point 1a for the sequence depicted below (see US20040176380). The chloro at position 4 of compound A is displaced with an aminoester in acetone (or hexane) to give B. Reduction of the nitro group, followed by in situ intramolecular cyclisation gives compound 1a.

Scheme 2

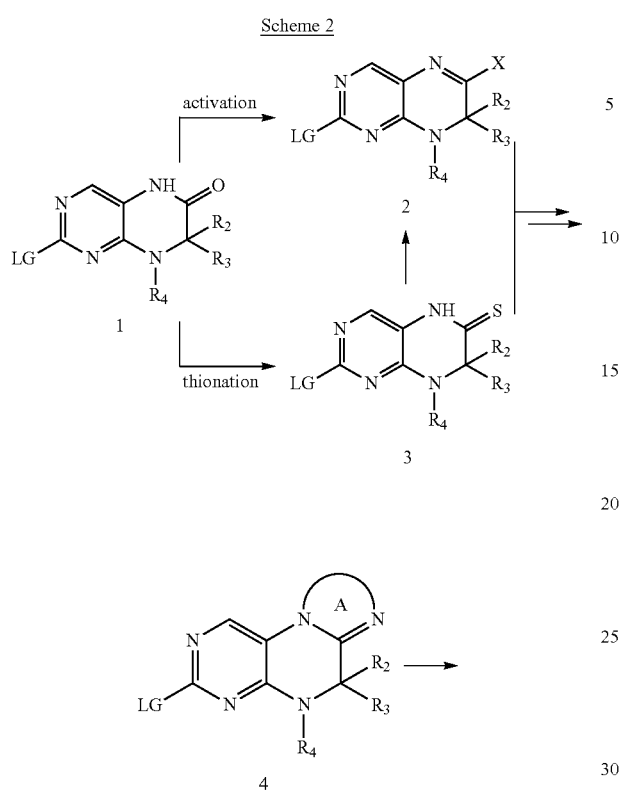

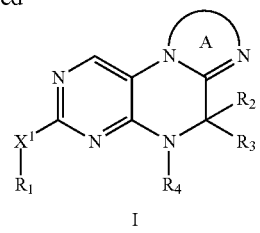

I

Scheme 2 above shows a general synthetic route for preparing compounds of this invention. The lactam functional group in 1 (see US20040176380) where LG is a suitable leaving group is activated under known conditions to give compounds 2 (X can be, but not restricted to, halo, alkoxy and phosphate). Compound 2 is then engaged in a 1 to 2 step sequence (depending on ring A) to give compounds 4. Alternatively, the carbonyl amide in 1 can be transformed into a thiocarbonyl to provide thiolactam 3. Compound 3 is then transformed into compound 2 (X=alkylthio) or engaged directly in a 1 to 2 step sequence (depending on ring A) to give compounds 4. LG can finally be used as a handle for preparation of the compounds of formula I. In this last step LG can, for example, be displaced with amines or be engaged in known palladium assisted coupling reactions, e.g. Suzuki, Stille or Buchwald reactions.

Scheme 3

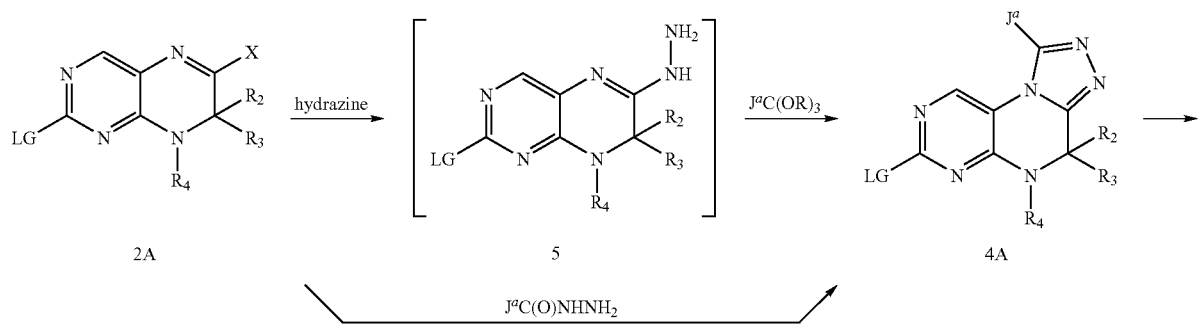

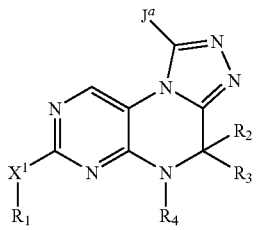

IA

Scheme 3 above shows a general synthetic route for preparing compounds of this invention where ring A is a triazole. The chloroimidate in 2A (X=Cl) or phosphate (X=OP(O)(OEt)2) in 2A reacts with hydrazine to give intermediate 5. Reaction of 5 with orthoesters $J^aC(OR)_3$ lead to compounds 4A where ring A is a triazole. Alternatively chloroimidate or phosphate (X=OP(O)(OEt)2) in 2A can be reacted with acylhydrazines $J^aC(O)NHNH_2$ to give directly compounds 4A where ring A is a triazole. LG can finally be used as a handle for preparation of the compounds of formula IA. In this last step LG can, for example, be displaced with amines or be engaged in palladium assisted coupling reactions known to one skilled in the art (e.g. Suzuki, Stille and Buchwald).

Similar approaches have been reported in the literature to transform amides $R^1$—NH—CO—$R^2$ into $R^1$-triazole-$R^2$, e.g.:

Trends in Het Chem, 8, 49-60, 2002
J Org Chem, 70(7), 2878-2880, 2005
Bioorg Med Chem Lett, 15(19), 4359-4362, 2005

Similar approaches have been reported in the literature to transform amides $R^1$—NH—CO—$R^2$ into $R^1$-tetrahydropyrimidine-$R^2$, e.g.:

J Am Chem Soc, 126 (7), 1971-1979, 2004
Angew Chemie, 43 (4), 478-482, 2004
J Am Chem Soc, 103 (14), 4186-4194, 1981
Indian J Chem, 12 (3), 263-269, 1974

One embodiment of this invention provides a process for preparing a compound of formula I:

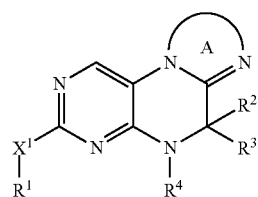

I

Scheme 4

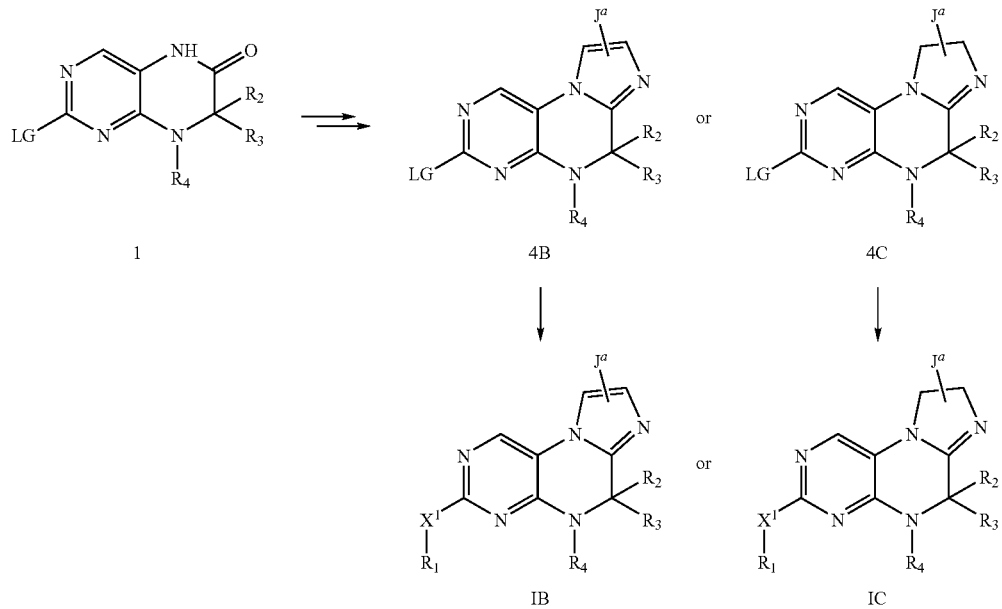

Scheme 4 above shows a general synthetic route for preparing compounds of this invention where ring A can be, but not restricted, an imidazole 1B, or an imidazoline 1C.

Similar approaches have been reported in the literature to transform amides $R^1$—NH—CO—$R^2$ into R1-imidazole-$R^2$, e.g.:

Afinidad, 45 (417), 443-446, 1988
J Org Chem, 59 (7), 5084-5087, 1994
Hey. Chim. Acta, 80 (3), 979-987, 1997
US2004132708
Bioorg Med Chem Lett, 12 (21), 3219-3222, 2002

Similar approaches have been reported in the literature to transform amides $R^1$—NH—CO—$R^2$ into $R^1$-imidazoline-$R^2$, e.g.:

Afinidad, 45 (417), 443-446, 1988
Het Chem, 19 (1), 193-200, 1982
J Org Chem, 50 (13), 2220-2224, 1985
Indian J Chem, 12 (3), 263-269, 1974
Heterocycles, 60 (6), 1425-1432, 2003 wherein
$X^1$, $R^1$, $R^2$, $R^3$, $R^4$, and Ring A are as defined herein.

The term "coupling reaction", as used herein, refers to a reaction in which a carbon-carbon bond is formed with the aid of a metal catalyst. Usually, one of the carbon atoms is bonded to a functional group (a "cross-coupling group") while the other carbon atom is bonded to a halogen. Examples of coupling reactions include, but are not limited to, Suzuki couplings, Stille couplings, Negishi and Buchwald couplings.

The term "coupling group", as used herein, refers to a functional group capable of reacting with another functional group (e.g. halo) in a coupling reaction to form a carbon-carbon ("C—C") bond or a carbon-nitrogen ("C—N") bond. In some embodiments, the C—C bond is formed between two aromatic groups.

The term "coupling condition", as used herein, refers to the chemical conditions (e.g. temperature, length of time of reaction, volume of solvent required) required in order to enable the coupling reaction to occur.

Examples of coupling groups and their respective coupling conditions include, but are not limited to, boronic acids and boronic esters with Suzuki coupling conditions, SnBu$_3$ with Stille coupling conditions, and ZnX with Negishi coupling conditions.

All three of these coupling conditions typically involve the use of a catalyst, a suitable solvent, and optionally a base. Suzuki coupling conditions involve the use of a palladium catalyst, a suitable base and a suitable solvent. Examples of suitable palladium catalysts include, but are not limited to, PdCl$_2$(PPh$_3$)$_2$, Pd(Ph$_3$)$_4$, and PdCl$_2$(dppf). Suitable bases include, but are not limited to, K$_2$CO$_3$ and Na$_2$CO$_3$. Suitable solvents include, but are not limited to, tetrahydrofuran, toluene, and ethanol.

Stille coupling conditions involve the use of a catalyst (usually palladium, but sometimes nickel), a suitable solvent, and other optional reagents. Examples of suitable catalysts include, but are not limited to, PdCl$_2$(PPh$_3$)$_2$, Pd(Ph$_3$)$_4$, and PdCl$_2$(dppf). Suitable solvents include, but are not limited to, tetrahydrofuran, toluene, and dimethylformamide.

Negishi coupling conditions involve the use of a catalyst (palladium or nickel) and a suitable solvent. Examples of suitable catalysts include, but are not limited to Pd$_2$(dba)$_3$, Ni(PPh$_3$)$_2$Cl$_2$, PdCl$_2$(PPh$_3$)$_2$, and Pd(Ph$_3$)$_4$. Suitable solvents include, but are not limited to, tetrahydrofuran, toluene, and dimethylformamide. Suzuki, Stille, and Negishi conditions are known to one skilled in the art and are described in more detail in a variety of references, including "March's Advanced Organic Chemistry".

Buchwald coupling conditions involve the use of a palladium catalyst, a suitable base and a suitable solvent. Examples of suitable palladium catalysts include, but are not limite to, Pd(OAc)$_2$ with xanthphos, PdCl2(PPh$_3$)$_2$, Pd(Ph$_3$)$_4$, and PdCl$_2$(dppf). Suitable bases include, but are not limited to, Cs$_2$CO$_3$, K$_2$CO$_3$ and Na$_2$CO$_3$. Suitable solvents include, but are not limited to, dioxane, tetrahydrofuran, toluene, and ethanol.

As would be understood by one skilled in the art, coupling groups are formed from coupling groups precursors. A "coupling group precursor is a reagent or group of reagents used to form a cross-coupling group. Examples include, but are not limited to, bis(pinacolato)diborane for the formation of boronate esters, trimethylborates for the formation of boronic acids, Bu$_3$SnCl for the formation of stannanes, and ZnCl$_2$ for the formation zincates in Negishi coupling reactions. Examples of suitable coupling group formation conditions include, but are not limited to, making boronic esters via palladium-mediated catalysis; making boronic acids by hydrolyzing boronic esters; making stannanes via a two step process: 1) halogen metal exchange followed by 2) transmetallation with Bu3SnCl; and making zincates via a two step process: 1) halogen metal exchange followed by 2) addition of ZnCl$_2$.

Another aspect of this invention provides compounds that are inhibitors of protein kinases, and thus are useful for the treatment of the diseases, disorders, and conditions, along with other uses described herein. In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

The present invention provides compounds and compositions that are useful as inhibitors of protein kinases. In some embodiments, the protein kinases are PLK. In some embodiments, PLK1.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is a PLK inhibitor.

One aspect of the invention relates to a method of inhibiting protein kinase activity in a patient, which method comprises administering to the patient a compound of formula I, or a composition comprising said compound.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In some embodiments, said protein kinase in PLK. In other embodiments, said condition is selected from a proliferative disorder and a neurodegenerative disorder.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of PLK1, PLK2, PLK3, and PLK4 are set forth in the Examples below.

One aspect of this invention provides compounds that are useful for the treatment of diseases, disorders, and conditions characterized by excessive or abnormal cell proliferation. Such diseases include, a proliferative or hyperproliferative disease, and a neurodegenerative disease.

Examples of proliferative and hyperproliferative diseases include, without limitation, cancer.

The term "cancer" includes, but is not limited to the following cancers: breast; ovary; cervix; prostate; testis, genitourinary tract; oesophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; chronic myeloid leukemia (CML), and leukemia.

Examples of neurodegenerative diseases include, without limitation, Alzheimer's disease.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, said disease is a protein-kinase mediated condition. In some embodiments, said disease is a PLK-mediated disease.

The term "protein kinase-mediated condition", as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "PLK-mediated condition", as used herein means any disease or other deleterious condition in which PLK plays a role. Such conditions include, without limitation, a proliferative or hyperproliferative disease, or a neurodegenerative disease.

In another aspect of the present invention, pharmaceutically acceptable compositions are provided, wherein these compositions comprise any of the compounds as described herein, and optionally comprise a pharmaceutically acceptable carrier, adjuvant or vehicle.

In certain embodiments, these compositions optionally further comprise one or more additional therapeutic agents.

For example, chemotherapeutic agents or other anti-proliferative agents may be combined with the compounds of this invention to treat proliferative diseases and cancer.

Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a PLK-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In addition to the compounds of this invention, pharmaceutically acceptable derivatives or prodrugs of the compounds of this invention may also be employed in compositions to treat or prevent the above-identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, a PLK-mediated condition) comprising the step of administering to a patient one of the above-described pharmaceutical compositions. The term "patient", as used herein, means an animal, preferably a human.

In some embodiments, said method is used to treat or prevent a condition selected from a proliferative disorder, such as cancer, a neurodegenerative disorder, an autoimmune disorder, an inflammatory disorder, and an immunologically-mediated disorder. In some embodiments, said method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease described above.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm
Gradient: 0-100% acetonitrile+methanol 60:40 (20 mM Tris phosphate)
Flow rate: 1.5 mL/minute
Detection: 225 nm.

Mass spec. samples were analyzed on a MicroMass Quattro Micro mass spectrometer operated in single MS mode with electrospray ionization. Samples were introduced into the mass spectrometer using chromatography.

$^1$H-NMR spectra were recorded at 400 MHz using a Bruker DPX 400 instrument and reported in ppm δ. The following compounds of formula I were prepared and analyzed as follows.

Example 1

4-((R)-5-cyclopentyl-4-ethyl-4,5-dihydro-[1,2,4]triazolo[4,3-f]pteridin-7-ylamino)-3-methoxy-N-methylbenzamide (I-1)

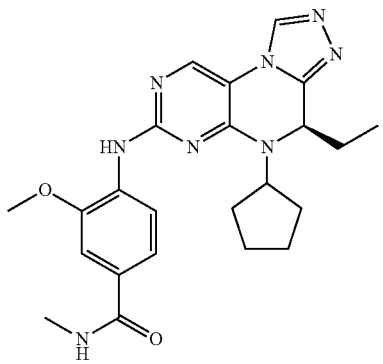

Method A: (R)-7-chloro-5-cyclopentyl-4-ethyl-4,5-dihydro-[1,2,4]triazolo[4,3-f]pteridine

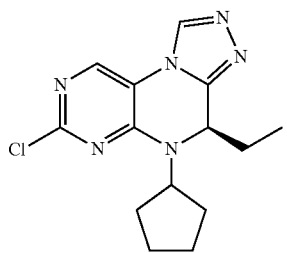

(R)-2-Chloro-8-cyclopentyl-7-ethyl-7,8-dihydropteridin-6(5H)-one (100 mg, 0.357 mmol) in phosphorus oxychloride (3.0 ml) was stirred at 110° C. for 3 hours then concentrated under reduced pressure. The residue was dissolved in anhydrous dichloromethane and added dropwise to 1.0 M hydrazine in THF (3.6 ml, 3.57 mmol). The mixture was stirred at RT overnight, taken into ethyl acetate and washed with aqueous sodium hydrogen carbonate, dried over magnesium sulphate and concentrated. The residue of crude hydrazide was dissolved in trimethyl orthoformate (2.0 ml) and stirred at 110° C. for 90 min. The mixture was concentrated under reduced pressure and purified by flash chromatography on silica gel eluting with ethyl acetate to give (R)-7-chloro-5-cyclopentyl-4-ethyl-4,5-dihydro-[1,2,4]triazolo[4,3-f]pteridine (68 mg, 63%) as a pale brown solid; $^1$H NMR (DMSO D$^6$) 0.75 (3H, t), 1.50-1.64 (2H, m), 1.80-2.08 (8H, m), 4.22-4.33 (1H, m), 5.28-5.35 (1H, m), 8.68 (1H, s), 9.35 (1H, s); MS (ES$^+$) 305.

Method B: 4-((R)-5-cyclopentyl-4-ethyl-4,5-dihydro-[1,2,4]triazolo[4,3-f]pteridin-7-ylamino)-3-methoxy-N-methylbenzamide (I-1)

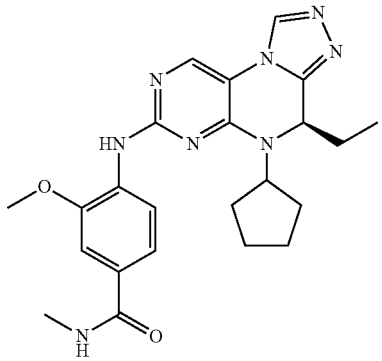

To a solution of (R)-7-chloro-5-cyclopentyl-4-ethyl-4,5-dihydro-[1,2,4]triazolo[4,3-f]pteridine (80 mg, 0.263 mmol) in a mixture ethanol/water (1/4, 5 mL) were added 4-amino-3-methoxy-N-methylbenzamide (72 mg, 0.394 mmol) followed by a catalytic amount of concentrated HCl (0.04 mL). The reaction mixture was stirred at 90° C. for 24 hours, then cooled to room temperature and basified with saturated aqueous solution of NaHCO$_3$. The mixture was extracted with ethyl acetate, the organic layer was dried (MgSO$_4$) and the residue purified by flash chromatography to give the title compound as a colourless solid (92 mg, 78% yield).

Submitted as a free base.

$^1$H NMR (DMSO D$^6$) 0.75 (3H, t), 1.43-1.60 (4H, m), 1.80-2.07 (6H, m), 2.80 (3H, d), 3.88 (3H, s), 4.19 (1H, m), 5.38 (1H, m), 7.50 (1H, d), 7.59 (1H, s), 7.83 (1H, d), 8.47 (1H, m), 8.67 (1H, s), 9.31 (1H, s), 9.40 (1H, br s); MS (ES$^+$) 449.

Example 2

4-((R)-5-cyclopentyl-4-ethyl-4,5-dihydro-[1,2,4]triazolo[4,3-f]pteridin-7-ylamino)-3-methoxy-N-(1-methylpiperidin-4-yl)benzamide (I-2)

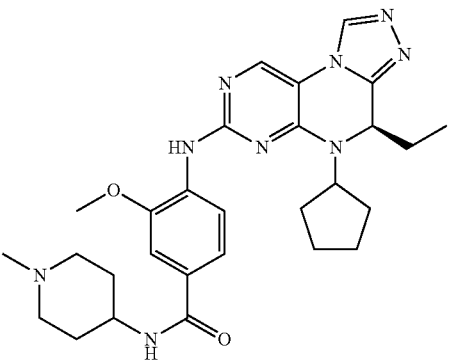

Prepared using method B, ubmitted as a free base.

$^1$H NMR (DMSO D$^6$) 0.73 (3H, t), 1.52-2.11 (15H, m), 2.25 (3H, s), 2.80-2.92 (2H, m), 3.27-3.32 (1H, m), 3.72-3.82 (1H, m), 4.37-4.47 (1H, m), 5.16-5.22 (1H, m), 7.46-7.51 (2H, m), 7.94 (1H, s), 8.12 (1H, d), 8.27 (1H, d), 8.61 (1H, s), 9.25 (1H, s); MS (ES$^+$) 532.

Example 3

4-((R)-5-cyclopentyl-4-ethyl-4,5-dihydro-[1,2,4]triazolo[4,3-f]pteridin-7-ylamino)-3-chlorobenzoic acid (I-3)

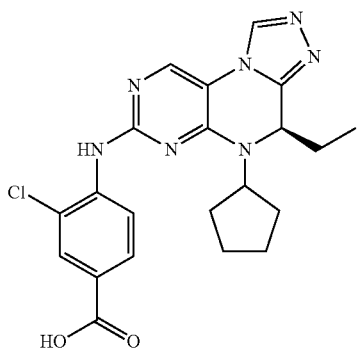

I-3

Prepared using method B, submitted as a free base. MS (ES+) 440; (ES−) 438.

Example 4

Method C: 4-((R)-5-cyclopentyl-4-ethyl-4,5-dihydro-[1,2,4]triazolo[4,3]pteridin-7-ylamino)-3-chloro-N-methylbenzamide (I-4)

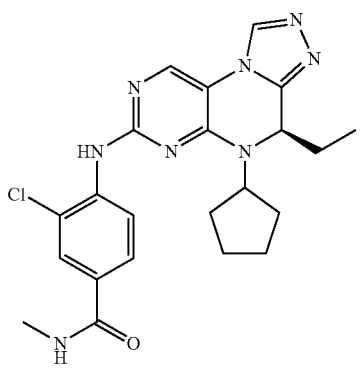

I-4

4-((R)-5-cyclopentyl-4-ethyl-4,5-dihydro-[1,2,4]triazolo[4,3-f]pteridin-7-ylamino)-3-chlorobenzoic acid (I-3) (27 mg) was dissolved in DMF (0.4 ml) and treated with carbonyl diimidazole (12 mg, 0.077 mmol) and the mixture stirred at RT for 90 min. The solution was cooled in an ice bath and methylamine gas bubbled in for 2 min. The mixture was stirred at RT for 2 hours, evaporated under reduced pressure and purified by chromatography to give 4-((R)-5-cyclopentyl-4-ethyl-4,5-dihydro-[1,2,4]triazolo[4,3-f]pteridin-7-ylamino)-3-chloro-N-methylbenzamide (15 mg) as a colourless solid.

Submitted as a free base.

$^1$H NMR (DMSO D$^6$) 0.71 (3H, t), 1.37-2.05 (10H, m), 2.80 (3H, s), 4.12-4.25 (1H, m), 5.20-5.31 (1H, m), 7.88 (1H, d), 8.00 (1H, d), 8.05 (1H, s), 8.50-8.55 (1H, m), 8.60 (1H, s), 8.97 (1H, br s), 9.35 (1H, s); MS (ES+) 453, (ES−) 451.

Example 5

4-((R)-5-cyclopentyl-4-ethyl-4,5-dihydro-[1,2,4]triazolo[4,3]pteridin-7-ylamino)-N,N,3-trimethylbenzamide (I-5)

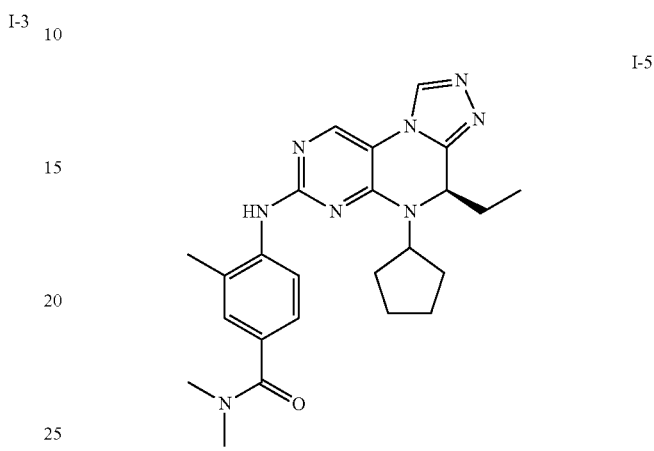

I-5

Method D: N,N,3-Trimethyl-4-nitrobenzamide

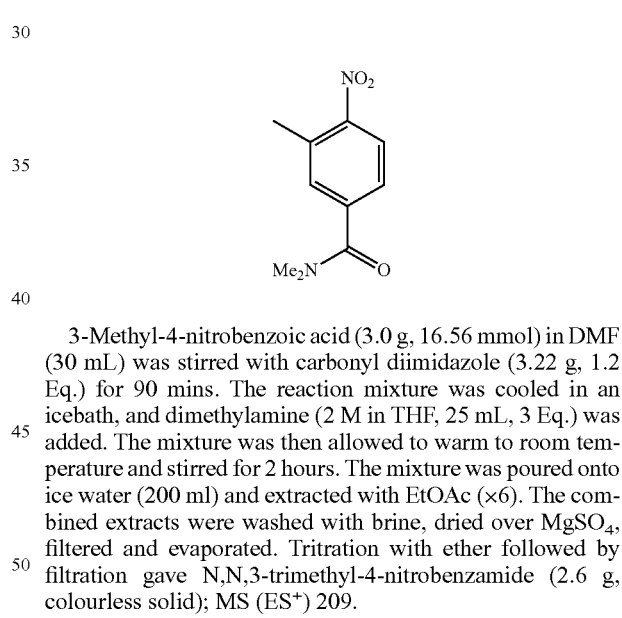

3-Methyl-4-nitrobenzoic acid (3.0 g, 16.56 mmol) in DMF (30 mL) was stirred with carbonyl diimidazole (3.22 g, 1.2 Eq.) for 90 mins. The reaction mixture was cooled in an icebath, and dimethylamine (2 M in THF, 25 mL, 3 Eq.) was added. The mixture was then allowed to warm to room temperature and stirred for 2 hours. The mixture was poured onto ice water (200 ml) and extracted with EtOAc (×6). The combined extracts were washed with brine, dried over MgSO$_4$, filtered and evaporated. Tritration with ether followed by filtration gave N,N,3-trimethyl-4-nitrobenzamide (2.6 g, colourless solid); MS (ES+) 209.

Method E: 4-Amino-N,N,3-trimethylbenzamide

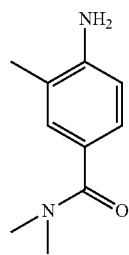

N,N,3-trimethyl-4-nitrobenzamide (0.6 g, 2.88 mmol) in methanol was hydrogenated using the H-cube apparatus (1.2 mL/min, RT, atmospheric pressure). After 45 minutes the reaction was complete. Removal of the solvent in vacuo gave 4-amino-N,N,3-trimethylbenzamide as a colourless solid (quantitative); MS (ES+) 179.

4-((R)-5-cyclopentyl-4-ethyl-4,5-dihydro-[1,2,4]triazolo[4,3]pteridin-7-ylamino)-N,N,3-trimethylbenzamide (I-5)

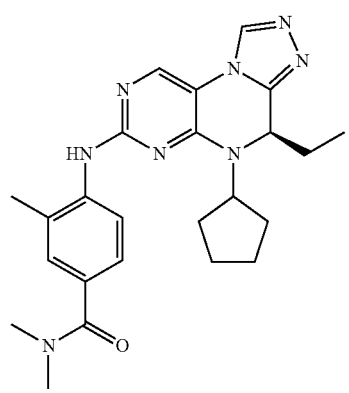

Prepared using method B, submitted as a free base.

$^1$H NMR (DMSO D$^6$) 0.69 (3H, t), 1.25-1.45 (4H, m), 1.70-2.05 (6H, m), 2.27(3H, s), 2.97 (6H, s), 4.08-4.15 (1H, m), 5.30-5.37 (1H, m), 7.29 (1H, d), 7.36 (1H, s), 7.46 (1H, d), 8.62 (1H, s), 9.33 (1H, s), 9.75 (1H, br s); MS (ES+) 447, (ES−) 445.

Example 6

4-((R)-5-cyclopentyl-4-ethyl-4,5-dihydro-[1,2,4]triazolo[4,3]pteridin-7-ylamino)-N,3-dimethylbenzamide (I-6)

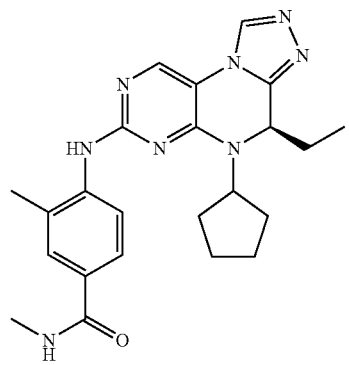

N,3-Dimethyl-4-nitrobenzamide

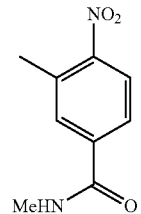

Prepared using method D

4-Amino-N,3-dimethylbenzamide

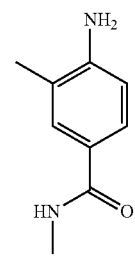

Prepared using method E, submitted as a free base.

4-((R)-5-cyclopentyl-4-ethyl-4,5-dihydro-[1,2,4]triazolo[4,3]pteridin-7-ylamino)-N,3-dimethylbenzamide (I-6)

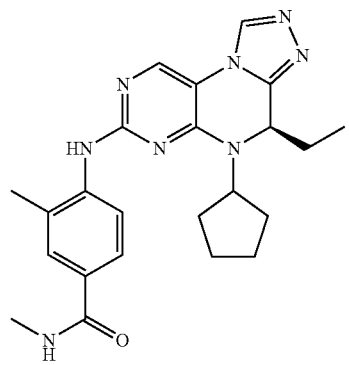

Prepared using method B, submitted as a free base.

$^1$H NMR (DMSO D$^6$) 0.68 (3H, t), 1.15-1.35 (4H, m), 1.65-2.05 (6H, m), 2.26 (3H, s), 2.78 (3H, s), 4.03-4.17 (1H, m), 5.36-5.43 (1H, m), 7.52 (1H, d), 7.76 (1H, d), 7.90 (1H, s), 8.52-8.57 (1H, m), 8.74 (1H, s), 9.39 (1H, s), 10.13 (1H, s); MS (ES+) 433, (ES−) 431.

Example 7

4-((R)-5-cyclopentyl-6-ethyl-5,6-dihydroimidazo[1,2)pteridin-3-ylamino)-3-methoxy-N-methylbenzamide (I-7)

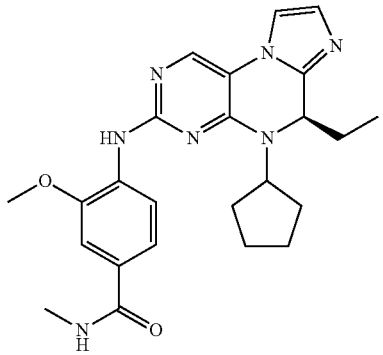

I-7

Method F: (R)-2-chloro-8-cyclopentyl-7-ethyl-7,8-dihydropteridin-6-amine

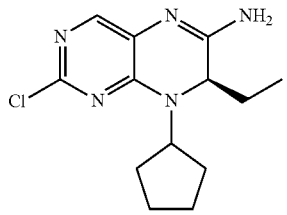

(R)-2-chloro-8-cyclopentyl-7-ethyl-7,8-dihydropteridin-6 (5H)-one (200 mg, 0.714 mmol) in POCl$_3$ (6 mL) was heated to 100 C for 4.5 hours. The solvent was removed in vacuo, and azeotroped twice with dry toluene. The residue was dissolved in dry CH$_2$Cl$_2$ (1.5 mL) and added dropwise to THF (5 mL) and in liquid NH$_3$ (4.2 g). The reaction mixture was stirred at RT over the weekend. The reaction mixture was poured onto ice water, and extracted with EtOAc×3. The combined organic extracts were concentrated in vacuo to give (R)-2-chloro-8-cyclopentyl-7-ethyl-7,8-dihydropteridin-6-amine as a brown oil (181 mg). MS (ES$^+$) 280, (ES$^-$) 278.

Method G: (R)-3-chloro-5-cyclopentyl-6-ethyl-5,6-dihydroimidazo[1,2-f]pteridine

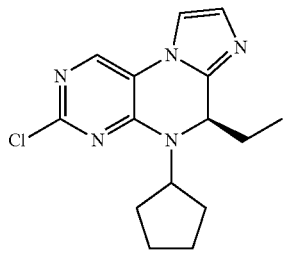

(R)-2-chloro-8-cyclopentyl-7-ethyl-7,8-dihydropteridin-6-amine (177 mg, 0.64 mmol) in MeOH (1.5 mL) treated with 50% aqueous chloroacetaldehyde (131 µL, 1.3 Eq.) and the reaction mixture heated to reflux for 6 hours. A further portion of 50% aq. chloroacetaldehyde (400 µL, 3.0 Eq.) was added, and the reaction mixture heated to 68° C. overnight. NaHCO$_3$ (aq. sat.) and EtOAc was added, and the aqueous was further extracted with EtOAc. The combined organic extracts were dried over MgSO$_4$, filtered and concentrated in vacuo.
MS (ES$^+$) 304.

4-((R)-5-cyclopentyl-6-ethyl-5,6-dihydroimidazo[1,2)pteridin-3-ylamino)-3-methoxy-N-methylbenzamide (I-7)

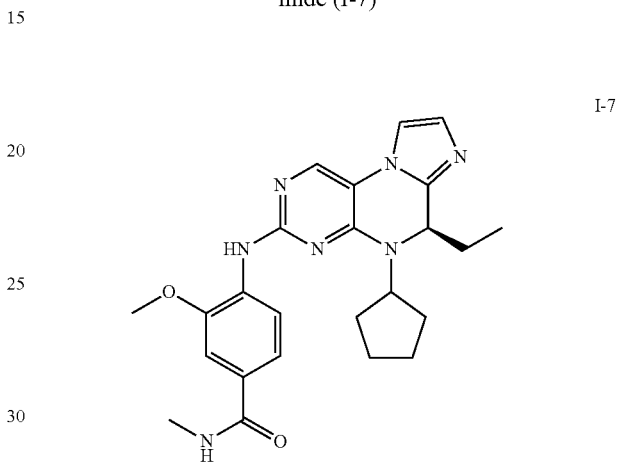

I-7

Prepared using method B, submitted as a free base.
$^1$H NMR (DMSO D$^6$) 0.66 (3H, t), 1.55-2.13 (10H, m), 2.79 (3H, d), 3.94 (3H, s), 4.35-4.48 (1H, m), 4.98-5.07 (1H, m), 7.13 (1H, s), 7.45-7.53 (2H, m), 7.79 (1H, s), 7.86 (1H, s), 8.25-8.38 (2H, m), 8.45 (1H, s); MS (ES$^+$) 448, MS (ES$^-$) 446.

Example 8

(R)-4-(5-cyclopentyl-4-ethyl-4,5-dihydro-[1,2,4]triazolo[4,3-f]pteridin-7-ylamino)-N-cyclopropyl-3-methoxybenzamide (I-8)

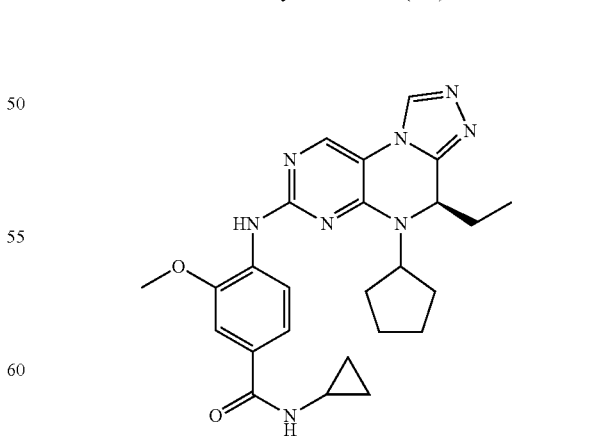

Prepared using method B, submitted as a free base.
$^1$H NMR DMSO D$^6$ 0.56-0.59 (2H, m), 0.68-0.73 (5H, m), 1.55-2.10 (10H, m), 2.82 (1H, m), 3.92 (3H, s), 4.42 (1H, m), 5.21 (1H, m), 7.46-7.48 (2H, m), 7.95 (1H, s), 8.26 (1H, d), 8.35 (1H, d), 8.59 (1H, s), 9.25 (1H, s); HPLC rt(min): 8.91; MS (ES+) 475, (ES−) 474.

Example 9

4-((R)-5-cyclopentyl-4-ethyl-4,5-dihydro-[1,2,4]triazolo[4,3-f]pteridin-7-ylamino)-3-methoxy-N-((R)-tetrahydrofuran-3-yl)benzamide (I-9)

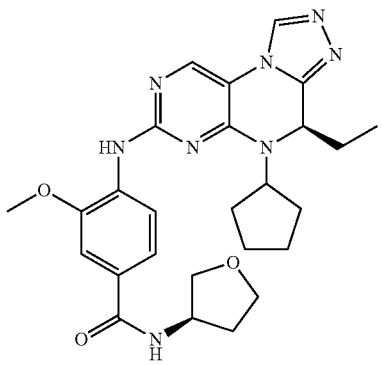

Prepared using method B, submitted as a free base.

$^1$H NMR DMSO D$^6$ 0.71 (3H, t), 1.55-2.20 (12H, m), 3.60 (1H, dd), 3.72 (1H, m), 3.87 (2H, m), 3.94 (3H, s), 4.40-4.53 (2H, m), 5.22 (1H, m), 7.51-7.54 (2H, m), 7.96 (1H, s), 8.30 (1H, m), 8.42 (1H, d), 8.60 (1H, s), 9.25 (1H, s); HPLC rt(min): 863; MS (ES+) 505.

Example 10

(R)-N-cyclopentyl-4-(5-cyclopentyl-4-ethyl-4,5-dihydro-[1,2,4]triazolo[4,3-f]pteridin-7-ylamino)-3-methoxybenzamide (I-10)

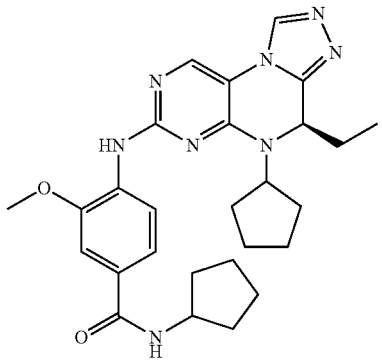

Prepared using method B, submitted as a free base.

$^1$H NMR DMSO D$^6$ 0.71 (3H, t), 1.48-1.65 (6H, m), 1.67-2.09 (12H, m), 3.93 (3H, s), 4.21-4.26 (1H, m), 4.42 (1H, quin), 5.20-5.22 (1H, m), 7.49-7.51 (2H, m), 7.95 (1H, s), 8.16 (1H, d), 8.29 (1H, d), 8.59 (1H, s), 9.25 (1H, s); HPLC rt(min): 9.76; MS (ES+) 503, (ES−) 501.

Example 11

(R)-4-(5-cyclopentyl-4-ethyl-4,5-dihydro-[1,2,4]triazolo[4,3-f]pteridin-7-ylamino)-N-cyclopropyl-benzamide (I-11)

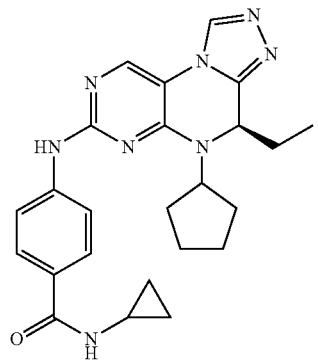

Prepared using method B, submitted as a free base.

$^1$H NMR DMSO D$^6$ 0.53-0.57 (2H, m), 0.63-0.73 (5H, m), 1.59-1.99 (9H, m), 2.06-2.15 (1H, m), 2.79-2.83 (1H, m), 4.48-4.55 (1H, m), 5.21 (1H, dd), 7.73.7.80 (4H, m), 8.26 (1H, d), 8.60 (1H, s), 9.25 (1H, s), 9.65 (1H, s); HPLC rt(min): 8.36; MS (ES+) 445, (ES−) 443.

Example 12

(4-((R)-5-cyclopentyl-4-ethyl-4,5-dihydro-[1,2,4]triazolo[4,3-f]pteridin-7-ylamino)-3-methoxyphenyl)((S)-3-fluoropyrrolidin-1-yl)methanone (I-12)

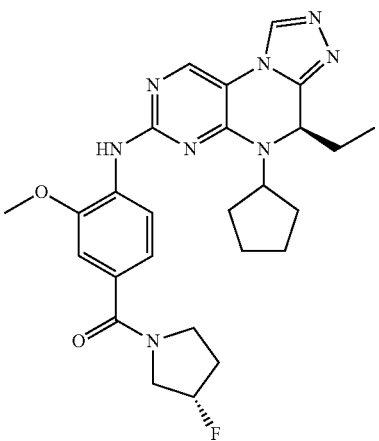

Prepared using method B, submitted as a free base.

$^1$H NMR DMSO D$^6$ 0.70 (3H, t), 1.50-1.62 (2H, m), 1.69-2.23 (10H, m), 3.53-3.84 (4H, m), 3.90 (3H, s), 4.38 (1H, t), 5.20 (1H, dd), 5.40 (1H, dd), 7.15 (1H, d), 7.20 (1H, d), 7.99

(1H, s), 8.20 (1H, s), 8.57 (1H, s), 9.25 (1H, s); HPLC rt(min): 8.94; MS (ES+) 507, (ES−) 505.

Example 13

(R)-4-(5-cyclopentyl-4-ethyl-1-methyl-4,5-dihydro-[1,2,4]triazolo[4,3-f]pteridin-7-ylamino)-N-cyclopropyl-3-methoxybenzamide (I-13)

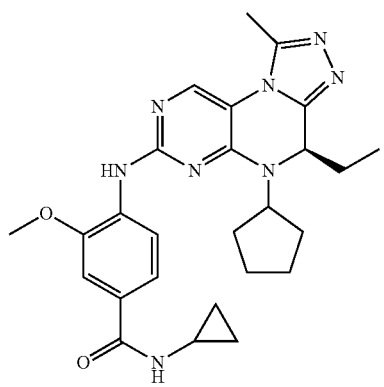

Prepared using method B, submitted as a free base.

$^1$H NMR DMSO D$^6$ 0.55-0.60 (2H, m), 0.69-0.78 (5H, m), 1.55-2.10 (10H, m), 2.68 (3H, s), 2.82 (1H, m), 3.93 (3H, s), 4.48 (1H, quint), 5.01 (1H, dd), 7.46-7.49 (2H, m), 7.94 (1H, s), 8.30 (1H, d), 8.35 (1H, d), 8.45 (1H, s); HPLC rt(min): 9.12; MS (ES+) 490, (ES−) 488.

Example 14

(R)-4-(5-cyclopentyl-4-ethyl-4,5-dihydro-[1,2,4]triazolo[4,3-f]pteridin-7-ylamino)-N-cyclopropyl-3-fluorobenzamide (I-14)

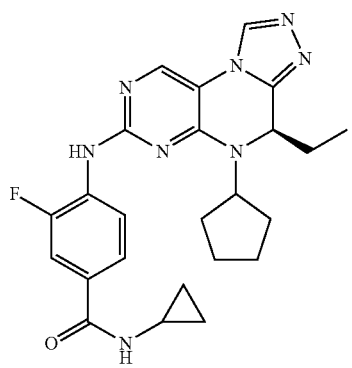

Prepared using method C, submitted as a free base.

$^1$H NMR DMSO D$^6$ 0.55-0.59 (2H, m), 0.67-0.73 (5H, m), 1.46-1.95 (10H, m), 2.84 (1H, m), 4.30 (1H, quint), 5.18 (1H, dd), 7.64-7.70 (2H, m), 7.91 (1H, t), 8.41 (1H, d), 8.55 (1H, s), 9.02 (1H, s), 9.24 (1H, s); HPLC rt(min): 8.58; MS (ES+) 464, (ES−) 462.

Example 15

(R)-5-(5-cyclopentyl-4-ethyl-4,5-dihydro-[1,2,4]triazolo[4,3-f]pteridin-7-ylamino)-N-cyclopropylthiophene-2-carboxamide (I-15)

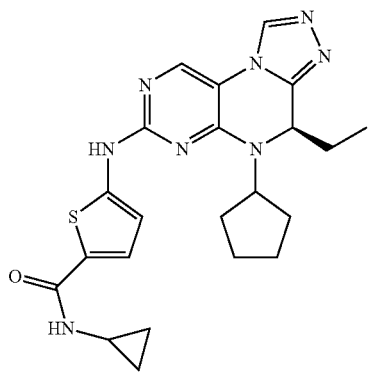

Prepared using method B, submitted as a free base.

$^1$H NMR DMSO D$^6$ 0.48-0.54 (2H, m), 0.63-0.74 (5H, m), 1.65-1.95 (10H, m), 2.74 (1H, m), 4.83 (1H, br s), 5.24 (1H, dd), 7.58 (1H, d), 7.47 (1H, d), 8.14 (1H, d), 8.63 (1H, s), 9.24 (1H, s), 10.83 (1H, br s); HPLC rt(min): 8.17; MS (ES+) 452, (ES−) 450.

Example 16

(R)-4-(5-cyclopentyl-4-ethyl-4,5-dihydro-[1,2,4]triazolo[4,3-f]pteridin-7-ylamino)-3-fluoro-N-methylbenzamide (I-16)

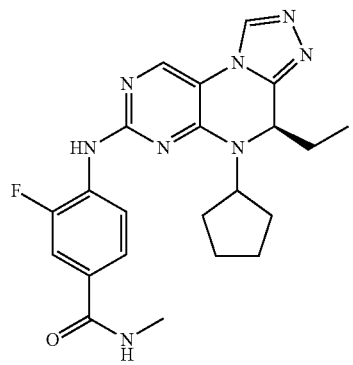

Prepared using method C, submitted as a mesylate salt.
Method H: Mesylate Formation The free base (38.2 mg, 0.088 mmol) was dissolved in hot methanol (3 ml) and treated with methane sulfonic acid (5.68 μL, 0.088 mmol), evaporated under reduced pressure and azeotroped three times with diethyl ether. The residue was triturated with ether and filtered to give the methane sulfonate salt (50.4 mg).

$^1$H NMR DMSO D$^6$ 0.69 (3H, t), 1.35-1.55 (4H, m), 1.70-2.0 (6H, m), 2.33 (3H, s), 2.79 (3H, d), 4.24 (1H, quint), 5.25

(1H, dd), 7.69-7.73 (2H, m), 7.84 (1H, t), 8.48 (1H, q), 8.57 (1H, s), 9.28 (1H, s), 9.39 (1H, s); HPLC rt(min): 8.07; MS (ES+) 438, (ES−) 436.

Example 17

(R)-4-(5-cyclopentyl-4-ethyl-4,5-dihydro-[1,2,4]triazolo[4,3-f]pteridin-7-ylamino)-N-(3,3-difluorocyclobutyl)-3-methoxybenzamide (I-17)

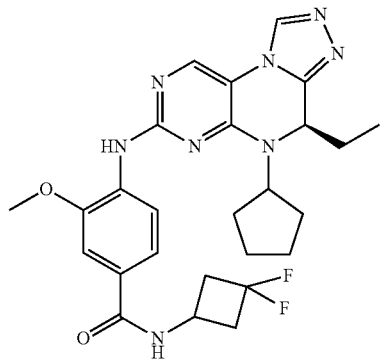

Prepared using method B, submitted as a mesylate salt (method H).

$^1$H NMR DMSO D$^6$ 0.70 (3H, t), 1.42-1.70 (4H, m), 1.75-2.04 (6H, m), 2.33 (3H, s), 2.70-2.85 (2H, m), 2.90-3.20 (2H, m), 3.92 (3H, s), 4.32 (2H, m), 5.33 (1H, dd), 7.52-7.56 (2H, m), 7.99 (1H, d), 8.59 (1H, s), 8.78 (1H, d), 8.98 (1H, br s), 9.30 (1H, s); HPLC rt(min): 9.35; MS (ES+) 526, (ES−) 524.

Example 18

(R)-4-(5-cyclopentyl-4-ethyl-4,5-dihydro-[1,2,4]triazolo[4,3-f]pteridin-7-ylamino)-N-ethyl-3-methoxybenzamide (I-18)

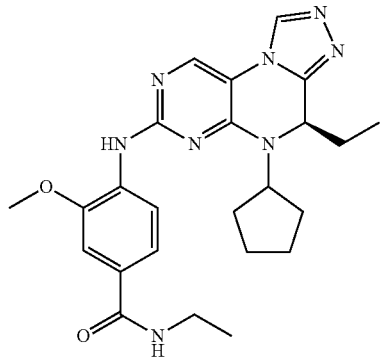

Prepared using method B, submitted as a mesylate salt (method H).

$^1$H NMR DMSO D$^6$ 0.70 (3H, t), 1.14 (3H, t), 1.45-1.67 (4H, m), 1.77-2.30 (6H, m), 2.31 (3H, s), 3.31 (2H, quint), 3.91 (3H, s), 4.32 (1H, quint), 5.32 (1H, dd), 7.52 (1H, dd), 7.56 (1H, d), 7.98 (1H, br d), 8.47 (1H, t), 8.58 (1H, s), 8.85 (1H, br s), 9.29 (1H, s); HPLC rt(min): 8.94; MS (ES+) 463, (ES−) 461.

Example 19

(R)-4-(5-cyclopentyl-4-ethyl-4,5-dihydro-[1,2,4]triazolo[4,3-f]pteridin-7-ylamino)-N-ethyl-3-fluorobenzamide (I-19)

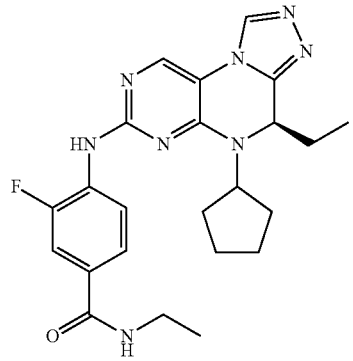

Prepared using method C, submitted as a mesylate salt (method H).

$^1$H NMR DMSO D$^6$ 0.70 (3H, t), 1.13 (3H, t), 1.38-1.55 (4H, m), 1.75-2.00 (6H, m), 2.32 (3H, s), 3.29 (2H, quint), 4.23 (1H, quint), 5.27 (1H, dd), 7.70-7.77 (2H, m), 7.83 (1H, t), 8.51 (1H, t), 8.57 (1H, s), 9.29 (1H, s), 9.45 (1H, br s); HPLC rt(min): 8.64; MS (ES+) 452, (ES−) 450.

Example 20

(R)-5-cyclopentyl-4-ethyl-N-(2-fluoro-4-(trifluoromethyl)phenyl)-4,5-dihydro-[1,2,4]triazolo[4,3-f]pteridin-7-amine (I-20)

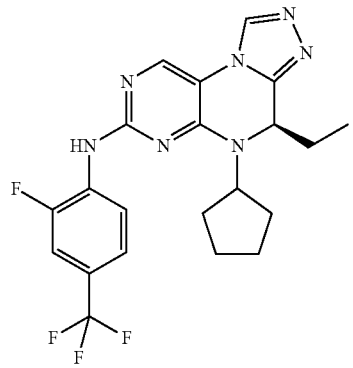

Prepared using method B, submitted as a mesylate salt (method H).

$^1$H NMR DMSO D$^6$ 0.69 (3H, m), 1.35-1.45 (4H, m), 1.73-2.00 (6H, m), 2.38 (3H, s), 4.16 (1H, quint), 5.31 (1H, dd), 7.63 (1H, d), 7.81 (1H, d), 7.91 (1H, t), 8.62 (1H, s), 9.34 (1H, s), 9.85 (1H, br s); HPLC rt(min): 10.44; MS (ES+) 448, (ES−) 446.

Example 21

Method I: (R)-4-(5-cyclopentyl-4-ethyl-4,5-dihydro-[1,2,4]triazolo[4,3-f]pteridin-7-ylamino)-N-methyl-3-(trifluoromethyl)benzamide (I-21)

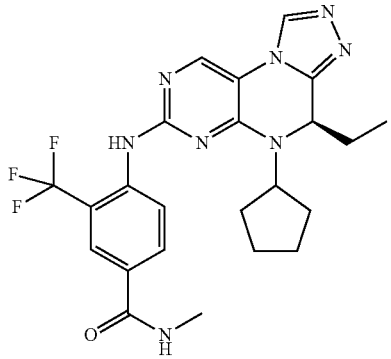

A mixture of (R)-7-chloro-5-cyclopentyl-4-ethyl-4,5-dihydro-[1,2,4]triazolo[4,3-f]pteridine (100 mg, 0.329 mmol), 4-amino-3-trifluoromethyl-N-methylbenzamide, palladium acetate (6 mg), cesium carbonate (214 mg, 0.658 mmol) and xanthphos (20 mg) in dioxane (4 ml) was stirred at 150° C. in a microwave for 1 hour. The mixture was diluted with ethyl acetate and washed with aqueous sodium hydrogen carbonate solution, dried over magnesium sulfate and concentrated. The residue was purified by chromatography on silica gel eluting with 0-12% methanol/ethyl acetate to give 4-((R)-5-cyclopentyl-4-ethyl-4,5-dihydro-[1,2,4]triazolo[4,3-f]pteridine-7-ylamino)-3-trifluoromethyl-N-methylbenzamide as a colourless glass (70 mg, 46%).

Submitted as a mesylate salt (method H).

$^1$H NMR DMSO $D^6$ 0.67 (3H, t), 0.96-1.35 (4H, m), 1.60-2.00 (6H, m), 2.34 (3H, s), 2.83 (3H, d), 3.90-4.03 (1H, m), 5.25-5.32 (1H, m), 7.82 (1H, d), 8.19 (1H, d), 8.26 (1H, s), 8.57 (1H, s), 8.75 (1H, d), 9.30 (1H, s), 9.46-9.66 (1H, br s); HPLC rt(min): 8.94; MS (ES$^+$) 487.

Example 22

(R)-5-cyclopentyl-4-ethyl-N-phenyl-4,5-dihydro-[1,2,4]triazolo[4,3-f]pteridin-7-amine (I-22)

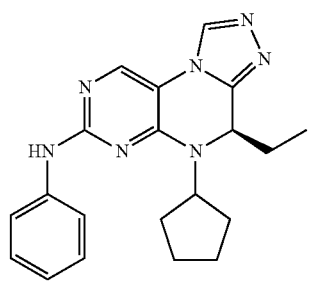

Prepared using method B, submitted as a free base.

$^1$H NMR DMSO $D^6$ 0.69-0.73 (3H, m), 1.59 (2H, m), 1.66-1.91 (7H, m), 2.06 (1H, m), 4.48 (1H, m), 5.18 (1H, m), 6.94 (1H, m), 7.25-7.28 (2H, m), 7.69-7.71 (2H, m), 8.55 (1H, s), 9.23 (1H, s), 9.37 (1H, s); HPLC rt(min): 9.75; MS (ES$^+$) 362, (ES$^-$) 360.

Example 23

(R)-5-cyclopentyl-4-ethyl-N-(pyridin-4-yl)-4,5-dihydro-[1,2,4]triazolo[4,3-f]pteridin-7-amine (I-23)

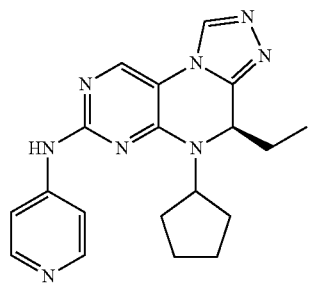

Prepared using method I, submitted as a free base.

$^1$H NMR DMSO $D^6$ 0.70-0.74 (3H, m), 1.62-1.63 (2H, m), 1.72-1.93 (7H, m), 2.11 (1H, m), 4.54 (1H, m), 5.23 (1H, m), 7.72 (2H, d), 8.33 (2H, d), 8.64 (1H, s), 9.27 (1H, s), 9.83 (1H, s); HPLC rt(min): 8.70; MS (ES$^+$) 363, (ES$^-$) 361.

Example 24

(R)-4-(5-cyclopentyl-4-ethyl-4,5-dihydro-[1,2,4]triazolo[4,3-f]pteridin-7-ylamino)-3-(difluoromethyl)-N-methylbenzamide (I-24)

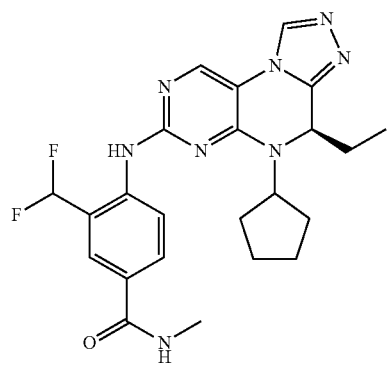

Prepared using method I, submitted as a mesylate salt (method H).

$^1$H NMR DMSO $D^6$ 0.69 (3H, t), 1.17-1.34 (4H, m), 1.71-1.89 (6H, m), 2.33 (3H, s), 2.81 (3H, d), 4.07-4.11 (1H, m), 5.27-5.29 (1H, m), 7.25 (1H, t), 7.70 (1H, d), 8.04 (1H, d), 8.15 (1H, s), 8.59 (1H, s), 8.63-8.65 (1H, m), 9.31 (1H, s), 9.60-9.64 (1H, m); HPLC rt(min): 8.28; MS (ES⁺) 469, (ES⁻) 467.

Example 25

(R)-5-cyclopentyl-4-ethyl-N-(pyridin-3-yl)-4,5-dihydro-[1,2,4]triazolo[4,3-f]pteridin-7-amine (I-25)

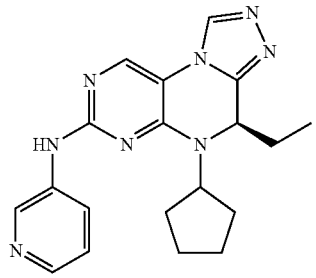

Prepared using method I, submitted as a free base.

¹H NMR DMSO D⁶ 0.69-0.73 (3H, m), 1.57-1.58 (2H, m), 1.71-1.90 (7H, m), 2.07 (1H, m), 4.48 (1H, m), 5.20 (1H, m), 7.30 (1H, m), 8.113-8.15 (2H, m), 8.58 (1H, m), 8.87 (1H, d), 9.25 (1H, s), 9.55 (1H, s); HPLC rt(min): 8.50; MS (ES⁺) 363, (ES⁻) 361.

Example 26

Method J: (R)-5-cyclopentyl-N-cyclopropyl-4-ethyl-4,5-dihydro-[1,2,4]triazolo[4,3-f]pteridin-7-amine (I-26)

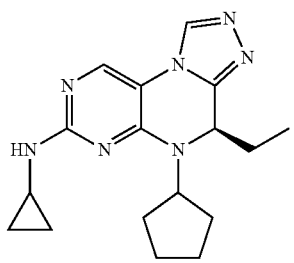

(R)-7-chloro-5-cyclopentyl-4-ethyl-4,5-dihydro-[1,2,4]triazolo[4,3-f]pteridine (70 mg, 0.23 mmol), cyclopropylamine (0.5 ml, 7.18 mmol), DIPEA (0.16 ml, 0.918 mmol) in ″BuOH (2 ml) were heated in a sealed tube in the microwave at 140° C. for 90 minutes. The reaction mixture was concentrated in vacuo, and purified by reverse phase preparative HPLC [Waters Sunfire C18, 10 M, 100 Å column, gradient 10%-95% B (solvent A: 0.05% TFA in water; solvent B: CH₃CN) over 16 minutes at 25 mL/min] to afford the title compound as an off-white powder. The free base was generated using a bicarbonate resin, and was freeze-dried to give the title compound as a colourless solid (25.6 mg, 34% yield)

Submitted as a free base.

¹H NMR DMSO D⁶ 0.46 (2H, m), 0.62-0.63 (2H, m), 0.67-0.71 (3H, m), 1.49 (2H, m), 1.60-2.00 (8H, m), 2.64 (1H, m), 4.22 (1H, br s), 5.11 (1H, m), 7.17 (1H, m), 8.38 (1H, s) 9.16 (1H, s); HPLC rt(min): 9.15; MS (ES⁺) 326, (ES⁻) 324.

Example 27

Method K: (R)-5-cyclopentyl-4-ethyl-4,5-dihydro-[1,2,4]triazolo[4,3-f]pteridin-7-amine (I-27)

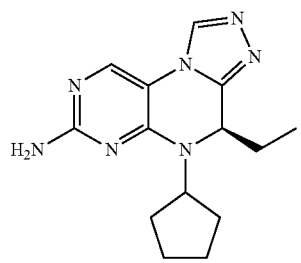

A solution of (R)-7-chloro-5-cyclopentyl-4-ethyl-4,5-dihydro-[1,2,4]triazolo[4,3-f]pteridine (500 mg, 1.64 mmol) in ammonium hydroxide (10 ml) was heated under microwave irradiation at 140° C. for 30 minutes. The solvent was removed under reduced pressure and cold water (5 mL) was added. The resulting light brown solid was filtered under vacuum and washed with cold water to give the title compound (170 mg, 36% yield).

Submitted as a free base.

¹H NMR DMSO D⁶ 0.69 (3H, t), 1.48-2.01 (10H, m), 4.40 (1H, dt), 5.06 (1H, dd), 6.40 (2H, s), 8.35 (1H, s), 9.15 (1H, s); HPLC rt(min): 7.43; MS (ES⁺) 286.

Example 28

Method L: (R)-5-cyclopentyl-4-ethyl-N-(pyridin-3-yl)-4,5-dihydro-[1,2,4]triazolo[4,3-f]pteridin-7-amine (I-28)

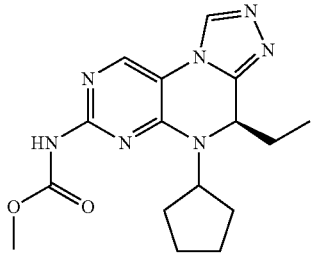

To (R)-5-cyclopentyl-4-ethyl-4,5-dihydro-[1,2,4]triazolo[4,3-f]pteridin-7-amine (50 mg, 0.175 mmol) in DMF (1 ml) at 0° C. was added sodium hydride (60% in mineral oil, 7.7 mg, 0.193 mmol). The reaction mixture was stirred for 10 minutes, then methyl chloroformate (13.6 μL, 0.175 mmol) was added. The reaction was allowed to warm up to room temperature and was stirred for 18 hours. Ammonium chloride (5 ml, sat. aq. soln.) was added and extracted with EtOAc (3×10 ml). The combined organics were washed with brine (10 ml), dried over MgSO₄, filtered and the solvent removed under vacuum. The crude product was purified by reverse phase preparative HPLC [Waters Sunfire C18, 10 M, 100 Å column, gradient 10%-95% B (solvent A: 0.05% TFA in water; solvent B: CH₃CN) over 16 minutes at 25 mL/min] to afford the title compound as an off-white powder (25 mg, 31%).

Submitted as a trifluoroacetic acid salt.

¹H NMR DMSO D⁶ 0.69 (3H, t), 1.47-1.63 (2H, m), 1.78-2.18 (8H, m), 3.70 (3H, s), 4.28 (1H, dt), 5.30 (1H, dd), 8.58 (1H, s), 9.34 (1H, s), 10.69 (1H, br s); HPLC rt(min): 7.62; MS (ES⁺) 344, (ES⁻) 342.

Example 29

(R)-4-(5-cyclobutyl-4-ethyl-4,5-dihydro-[1,2,4]triazolo[4,3-f]pteridin-7-ylamino)-3-methoxy-N-methylbenzamide (I-29)

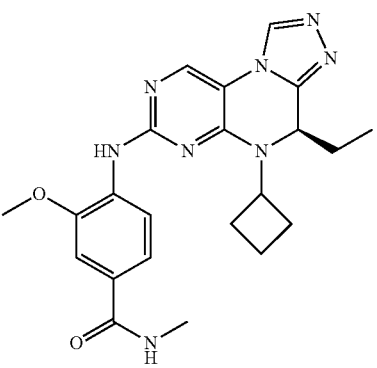

Prepared using method B, submitted as a mesylate salt (method H).

¹H NMR DMSO D⁶ 0.72 (3H, t), 1.63-1.87 (4H, m), 2.10-2.50 (4H, m), 2.31 (3H, s), 2.80 (3H, d), 3.92 (3H, s), 4.47 (1H, quint), 5.32 (1H, dd), 7.50-7.55 (2H, m), 8.11 (1H, br d), 8.43 (1H, br q), 8.59 (1H, s), 8.82 (1H, br s), 9.30 (1H, s); HPLC rt(min): 8.32; MS (ES⁺) 435, (ES⁻) 433.

Example 30

(R)-4-(5-cyclopentyl-4-ethyl-4,5-dihydro-[1,2,4]triazolo[4,3-f]pteridin-7-ylamino)-3-(methoxymethyl)-N-methylbenzamide (I-30)

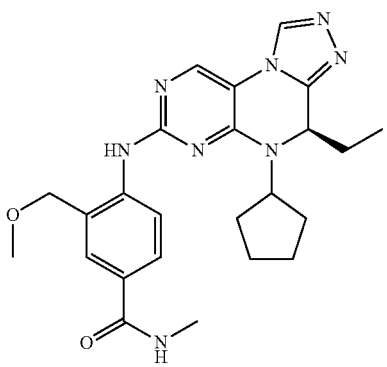

Prepared using method I, submitted as a mesylate salt (method H).

¹H NMR DMSO D⁶ 0.69 (3H, t), 1.31-1.50 (4H, m), 1.72-2.03 (6H, m), 2.33 (3H, s), 2.79 (3H, d), 3.32 (3H, s), 4.09-4.20 (1H, m), 4.52 (2H, s), 5.28-5.35 (1H, m), 7.80-7.87 (2H, m), 7.90 (1H, s), 8.41-8.49 (1H, m), 8.58 (1H, s), 9.20-9.35 (1H, br s), 9.30 (1H, s); HPLC rt(min): 8.39; MS (ES⁺) 463, (ES⁻) 461.

Example 31

(R)-N-benzyl-5-cyclopentyl-4-ethyl-4,5-dihydro-[1,2,4]triazolo[4,3-f]pteridin-7-amine (I-31)

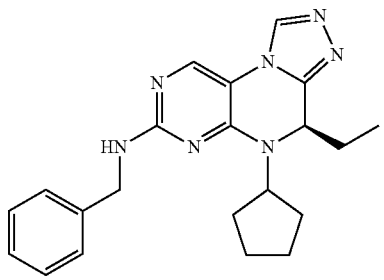

Prepared using method J, submitted as a free base.

¹H NMR DMSO D⁶ 0.65-0.69 (3H, m), 1.48 (2H, m), 1.64-1.89 (8H, m), 4.10 (1H, m), 4.45 (2H, m), 5.07 (1H, m), 7.20 (1H, m), 7.28 (4H, m), 7.57 (1H, br s), 8.38 (1H, s), 9.14 (1H, s); HPLC rt(min): 9.77; MS (ES⁺) 376, (ES⁻) 374.

Example 32

(R)-5-cyclopentyl-4-ethyl-N-(4-(4-methylpiperazin-1-yl)phenyl)-4,5-dihydro-[1,2,4]triazolo[4,3-f]pteridin-7-amine (I-32)

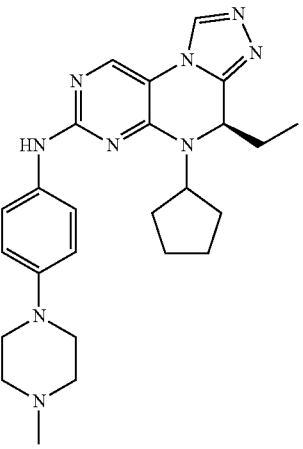

Prepared using method I, submitted as a free base.

¹H NMR DMSO D⁶ 0.70-0.72 (3H, m), 1.56 (2H, m), 1.74-2.02 (8H, m), 2.23 (3H, s), 2.50 (4H, m), 3.06 (4H, m), 4.43 (1H, m), 5.15 (1H, m), 6.86 (2H, d), 7.50 (2H, d), 8.49 (1H, s), 9.10 (1H, s), 9.20 (1H, s); HPLC rt(min): 9.02; MS (ES+) 460, (ES−) 458.

Example 33

(R)-5-cyclopentyl-N-(4-(difluoromethoxy)phenyl)-4-ethyl-4,5-dihydro-[1,2,4]triazolo[4,3-f]pteridin-7-amine (I-33)

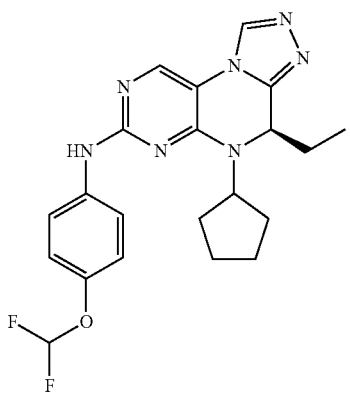

Prepared using method I, submitted as a free base.

$^1$H NMR DMSO D$^6$ 0.75 (3H, m), 1.59 (2H, m), 1.76-1.89 (8H, m), 2.07 (1H, m), 4.48 (1H, m), 5.18 (1H, m), 7.11 (2H, d), 7.72 (2H, d), 8.55 (1H, s), 9.23 (1H, s), 9.44 (1H, s); HPLC rt(min): 9.70; MS (ES+) 428, (ES−) 426.

Example 34

(R)-5-cyclopentyl-4-ethyl-N-(4-morpholinophenyl)-4,5-dihydro-[1,2,4]triazolo[4,3-f]pteridin-7-amine (I-34)

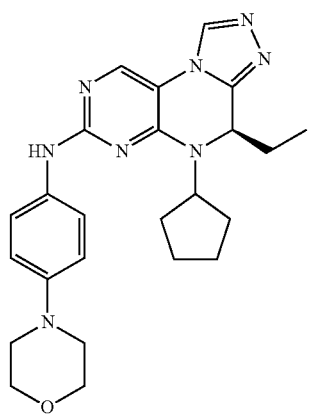

Prepared using method I, submitted as a free base.

$^1$H NMR DMSO D$^6$ 0.69-0.72 (3H, m), 1.57 (2H, m), 1.71-1.89 (7H, m), 2.00 (1H, m), 2.54 (4H, m), 3.72-3.75 (4H, m), 4.43 (1H, m), 5.16 (1H, m), 6.87 (2H, d), 7.52 (2H, d), 8.50 (1H, s), 9.12 (1H, s), 9.21 (1H, s); HPLC rt(min): 9.12; MS (ES+) 447, (ES−) 445.

Example 35

(R)-5-cyclopentyl-4-ethyl-N-(4-fluprophenyl)-4,5-dihydro-[1,2,4]triazolo[4,3-f]pteridin-7-amine (I-35)

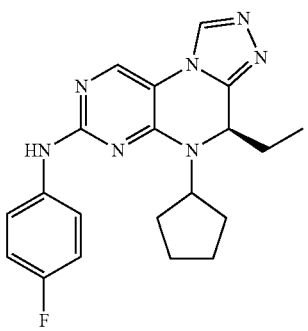

Prepared using method I, submitted as a free base.

$^1$H NMR DMSO D$^6$ 0.69-0.72 (3H, m), 1.60 (2H, m), 1.73-1.90 (7H, m), 2.06 (1H, m), 4.46 (1H, m), 5.19 (1H, m), 7.09 (2H, m), 7.67-7.70 (2H, m), 8.54 (1H, s), 9.23 (1H, s), 9.38 (1H, s); HPLC rt(min): 9.78; MS (ES+) 380, (ES−) 378.

Example 36

Method M: (R)-5-cyclopentyl-4-ethyl-N-methyl-4,5-dihydro-[1,2,4]triazolo[4,3-f]pteridin-7-amine (I-36)

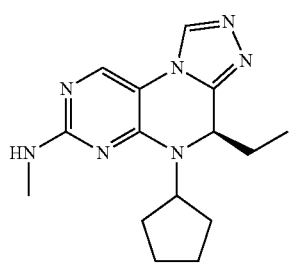

In a vial containing (R)-7-chloro-5-cyclopentyl-4-ethyl-4,5-dihydro-[1,2,4]triazolo[4,3-f]pteridine (70 mg, 0.23 mmol) was added a solution of methylamine in ethanol (2 mL, 2M soln.) The vessel was sealed then heated at 50° C. for 18 hours. After cooling, the solvent was removed under reduced pressure and the crude product was purified by reverse phase preparative HPLC [Waters Sunfire C18, 10 M, 100 Å column, gradient 10%-95% B (solvent A: 0.05% TFA in water; solvent B: CH$_3$CN) over 16 minutes at 25 mL/min]. The free base was obtained by passing the TFA salt in acetonitrile/water through a carbonate cartridge to afford the title compound as a white powder (42 mg, 61% yield).

Submitted as a free base.

$^1$H NMR DMSO D$^6$ 0.68 (3H, t), 1.47-2.03 (10H, m), 2.77 (3H, d), 4.24-4.32 (1H, m), 5.09 (1H, d), 6.86 (1H, bs), 8.38 (1H, s), 9.15 (1H, s); HPLC rt(min): 8.57; MS (ES+) 300, (ES−) 298.

Example 37

(R)-5-cyclopentyl-N,4-diethyl-4,5-dihydro-[1,2,4]triazolo[4,3-f]pteridin-7-amine (I-37)

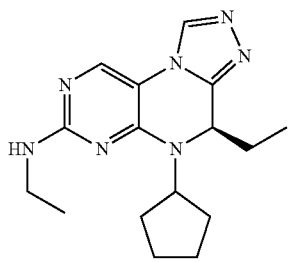

Prepared using method M, submitted as a free base.
$^1$H NMR DMSO D$^6$ 0.69 (3H, t), 1.10 (3H, t), 1.47-1.99 (10H, m), 3.26 (2H, dt), 4.27 (1H, br s), 5.09 (1H, d), 6.94 (1H, br s), 8.37 (1H, s), 9.15 (1H, s); HPLC rt(min): 9.14; MS (ES$^+$) 314, (ES$^-$) 312.

Example 38

(R)-N,5-dicyclopentyl-4-ethyl-4,5-dihydro-[1,2,4]triazolo[4,3-f]pteridin-7-amine (I-38)

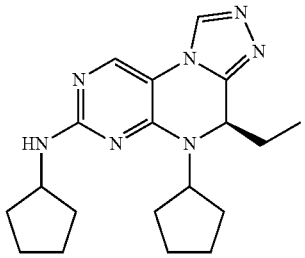

Prepared using method J, submitted as a free base.
$^1$H NMR DMSO D$^6$ 0.69 (3H, t), 1.43-2.00 (18H, m), 4.07-4.17 (1H, m), 4.17-4.34 (1H, m), 5.08 (1H, bs), 6.98 (1H, bs), 8.36 (1H, s), 9.14 (1H, s); HPLC rt(min): 10.2; MS (ES$^+$) 354, (ES$^-$) 352.

Example 39

(R)-N-(4-(1H-pyrazol-1-yl)phenyl)-5-cyclopentyl-4-ethyl-4,5-dihydro-[1,2,4]triazolo[4,3-f]pteridin-7-amine (I-39)

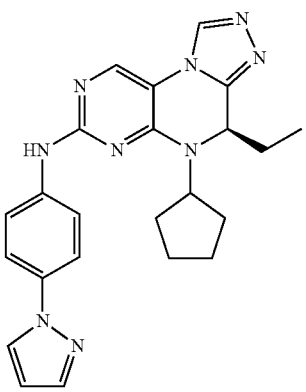

Prepared using method I, submitted as a trifluoroacetic acid salt.
$^1$H NMR DMSO D$^6$ 0.70 (3H, m), 1.58-1.59 (2H, m), 1.75-2.07 (7H, m), 2.33 (1H, m), 4.48 (1H, m), 5.22 (1H, m), 6.52 (1H, s), 7.71-7.81 (5H, m), 8.42 (1H, m), 8.58 (1H, s), 9.26 (1H, s), 9.64 (1H, s); HPLC rt(min): 9.32; MS (ES$^+$) 428, (ES$^-$) 426.

Example 40

(R)-5-cyclopentyl-4-ethyl-N-(6-(trifluoromethyl)pyridin-3-yl)-4,5-dihydro-[1,2,4]triazolo[4,3-f]pteridin-7-amine (I-40)

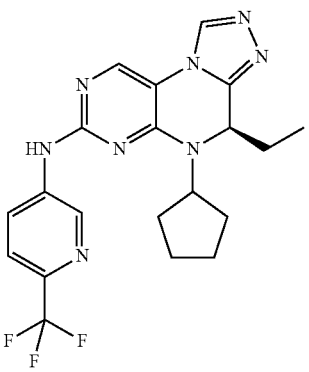

Prepared using method I, submitted as a free base.
$^1$H NMR DMSO D$^6$ 0.70 (3H, m), 0.70-0.74 (3H, m), 1.60-1.63 (2H, m), 1.71-1.92 (7H, m), 2.08 (1H, m), 4.51 (1H, m), 5.22 (1H, m), 7.82 (1H, d), 8.42 (1H, d), 8.64 (1H, s), 9.03 (1H, m), 9.27 (1H, s), 9.98 (1H, s); HPLC rt(min): 9.70; MS (ES$^+$) 431, (ES$^-$) 429.

Example 41

(R)-5-cyclopentyl-4-ethyl-N-(6-(4-methylpiperazin-1-yl)pyridin-3-yl)-4,5-dihydro-[1,2,4]triazolo[4,3-f]pteridin-7-amine (I-41)

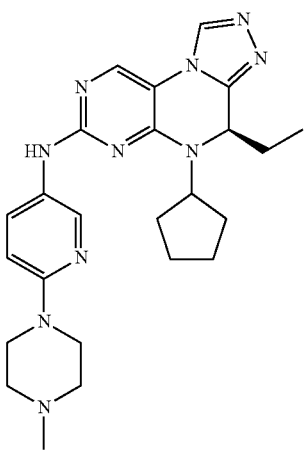

Prepared using method I, submitted as a free base.

$^1$H NMR DMSO D$^6$ 0.68-0.72 (3H, m), 1.53 (2H, m), 1.69-1.97 (8H, m), 2.23 (3H, s), 2.42 (4H, m), 3.40 (4H, m), 4.35 (1H, m), 5.14 (1H, m), 6.80 (1H, d), 7.79 (1H, m), 8.32 (1H, m), 8.48 (1H, s), 9.04 (1H, s), 9.20 (1H, s); HPLC rt(min): 8.70; MS (ES$^+$) 461, (ES$^-$) 459.

Example 42

(R)-5-cyclopentyl-4-ethyl-N-(4-(pyrrolidin-1-yl)phenyl)-4,5-dihydro-[1,2,4]triazolo[4,3-f]pteridin-7-amine (I-42)

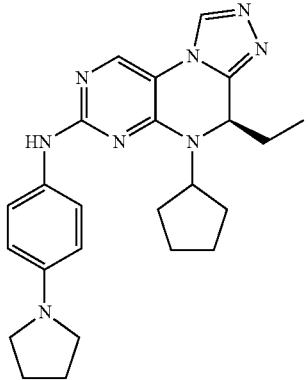

Prepared using method I, submitted as a free base.

$^1$H NMR DMSO D$^6$ 0.69-0.72 (3H, m), 1.54 (2H, m), 1.60-1.81 (8H, m), 1.89-1.94 (4H, m), 3.19 (4H, m), 4.38 (1H, m), 5.13 (1H, m), 6.47-6.52 (2H, m), 7.42 (2H, d), 8.46 (1H, s), 8.91 (1H, s), 9.19 (1H, s); HPLC rt(min): 10.44; MS (ES$^+$) 431, (ES$^-$) 429.

Example 43

PLK1 Assay

Compounds of the present invention may be evaluated as inhibitors of human PLK kinase using the following assays.
Plk1 Inhibition Assay:

Compounds were screened for their ability to inhibit Plk1 using a radioactive-phosphate incorporation assay. Assays were carried out in a mixture of 25 mM HEPES (pH 7.5), 10 mM MgCl$_2$, and 1 mM DTT. Final substrate concentrations were 50 μM [γ-33P]ATP (136 mCi 33P ATP/mmol ATP, Amersham Pharmacia Biotech/Sigma Chemicals) and 10 μM peptide (SAM68 protein Δ332-443). Assays were carried out at 25° C. in the presence of 15 nM Plk1 (A20-K338). An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 50 μM).

The reaction was stopped after 60 minutes by the addition of 100 μL 0.14M phosphoric acid. A multiscreen phosphocellulose filter 96-well plate (Millipore, Cat no. MAPHN0B50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).
Plk1 Inhibition Assay:

Compounds were screened for their ability to inhibit Plk1 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 150 μM (350 μM for determining values of <1 nM) [γ-33P]ATP (115 mCi 33P ATP/mmol ATP, Amersham Pharmacia Biotech/Sigma Chemicals) and 300 μM (450 μM for determining values of <1 nM) peptide (KKKIS-DELMDATFADQEAK) SEQ. ID NO. 1. Assays were carried out at 25° C. in the presence of 4 nM (1 nM for determining values of <1 nM) Plk1. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 150 μM (350 μM for determining values of <1 nM))).

The reaction was stopped after 90 minutes (240 minutes for determining values of <1 nM) by the addition of 100 μL 0.14M phosphoric acid. A multiscreen phosphocellulose filter 96-well plate (Millipore, Cat no. MAPHN0B50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

In general, compounds of the invention are effective for the inhibition of Plk1. The following compounds showed Ki below 10 nM in the radioactive incorporation assay: I-1, I-2, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-29, I-30, I-32, I-33, I-34, I-35, I-39, I-41, I-42. The following compounds showed Ki between 10 nM and 100 nM in the radioactive incorporation assay: I-31, I-40. The following compounds showed Ki between 100 nM and 4 μM in the radioactive incorporation assay: I-26, I-27, I-28, I-36, I-37, I-38.
Plk2 Inhibition Assay:

Compounds were screened for their ability to inhibit Plk2 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 200 μM [γ-33P]ATP (57 mCi 33P ATP/mmol ATP, Amersham Pharmacia Biotech/Sigma Chemicals)

and 300 µM peptide (KKKISDELMDATFADQEAK) SEQ. ID NO. 2. Assays were carried out at 25° C. in the presence of 25 nM Plk2. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 200 µM).

The reaction was stopped after 90 minutes by the addition of 100 µL 0.14M phosphoric acid. A multiscreen phosphocellulose filter 96-well plate (Millipore, Cat no. MAPHN0B50) was pretreated with 100 82 L 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Plk3 Inhibition Assay:

Compounds were screened for their ability to inhibit Plk3 using a radioactive-phosphate incorporation assay. Assays were carried out in a mixture of 25 mM HEPES (pH 7.5), 10 mM $MgCl_2$, and 1 mM DTT. Final substrate concentrations were 75 µM [γ-33P]ATP (60 mCi 33P ATP/mmol ATP, Amersham Pharmacia Biotech/Sigma Chemicals) and 10 µM peptide (SAM68 protein Δ332-443). Assays were carried out at 25° C. in the presence of 5 nM Plk3 (S38-A340). An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 75 µM).

The reaction was stopped after 60 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Plk4 Inhibition Assay:

Compounds were screened for their ability to inhibit Plk4 using a radioactive-phosphate incorporation assay. Assays were carried out in a mixture of 8 mM MOPS (pH 7.5), 10 mM $MgCl_2$, 0.1% BSA and 2 mM DTT. Final substrate concentrations were 15 µM [γ-33P]ATP (227 mCi 33P ATP/mmol ATP, Amersham Pharmacia Biotech/Sigma Chemicals) and 300 µM peptide (KKKMDATFADQ) SEQ. ID NO. 3. Assays were carried out at 25° C. in the presence of 25 nM Plk4. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 15 µM).

The reaction was stopped after 180 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

We claim:

1. A compound of formula I:

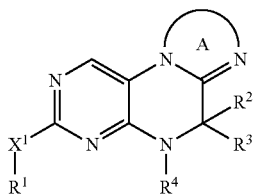

or a pharmaceutically acceptable salt thereof, wherein
Ring A is an imidazole ring wherein the ring is optionally substituted with $C_{1-6}$ haloalkyl, halo, $NO_2$, —OH, —CN or $C_{1-6}$ alkyl;
$X^1$ is —$NR^8$—
$R^1$ is H, $C_{1-10}$ aliphatic, $C_{3-10}$ cycloaliphatic, $C_{6-10}$ aryl, 5-10 membered heteroaryl, or 3-10 membered heterocyclyl, wherein said $R^1$ is optionally substituted with 0-5 $J^1$;
Each $R^2$ and $R^3$ is independently H, or $C_{1-3}$ alkyl;
$R^4$ is H, $C_{1-10}$ aliphatic, or $C_{3-10}$ cycloaliphatic, wherein said $R^4$ is optionally substituted with 0-5 $J^4$;
$R^8$ is H, $C_{1-6}$ aliphatic, $C_{3-8}$ cycloaliphatic, —C(O)R, —C(O)OR, or —C(O)NRR';
Each $J^1$ is independently $C_{1-6}$ haloalkyl, halo, $NO_2$, CN, Q, or -Z-Q, or two $J^1$ taken together can optionally form =O;
Each Z is independently $C_{1-6}$ aliphatic in which 0-3 —$CH_2$— units in said $C_{1-6}$ aliphatic are optionally replaced with —NR—, —O—, —S—, —C(O)—, —C(=NR)—, —C(=NOR)—, —S(O)—, or —$S(O)_2$—, wherein any non-replaced —$CH_2$— units in said $C_{1-6}$ aliphatic are optionally substituted with 0-2 $J^Z$;
Each Q is independently H, $C_{1-6}$ aliphatic, a 3-8-membered aromatic or non-aromatic monocyclic ring having 0-3 heteroatoms independently selected from O, N, and S, or an 8-12 membered aromatic or non-aromatic bicyclic ring system having 0-5 heteroatoms independently selected from O, N, and S, wherein each Q is independently optionally substituted with 0-5 $J^Q$;
Each $J^Z$ is independently halo, $C_{1-6}$ aliphatic, $C_{3-6}$ cycloaliphatic, $NO_2$, CN, OH, $NH_2$, $NH(C_{1-4}$ aliphatic), $N(C_{1-4}$ aliphatic$)_2$, —$O(C_{1-4}$ aliphatic), —$CO_2H$, —$CO_2(C_{1-4}$ aliphatic), —$O(haloC_{1-4}$ aliphatic), or halo ($C_{1-4}$ aliphatic);
Each $J^Q$, and $J^4$ is independently -M or -Y-M;
Each Y is independently an unsubstituted $C_{1-6}$ aliphatic in which 0-3 —$CH_2$— units in said $C_{1-6}$ aliphatic are optionally replaced with —NR—, —O—, —S—, —C(O)—, —S(O)—, or —$S(O)_2$—;
Each M is independently H, $C_{1-6}$ aliphatic, $C_{3-6}$ cycloaliphatic, halo($C_{1-4}$ aliphatic), O(halo$C_{1-4}$ aliphatic), 3-6 membered heterocyclyl, halo, $NO_2$, CN, OH, OR', SH, SR', $NH_2$, NHR', N(R')$_2$, COH, COR', $CO_2H$, $CO_2R'$, $CONH_2$, CONHR', CON(R')$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, or $NR'SO_2R'$;
Each R is independently H or unsubstituted $C_{1-6}$ aliphatic; and
Each R' is unsubstituted $C_{1-6}$ aliphatic, or two R' groups, together with the atom to which they are bound, form an unsubstituted 3-8 membered saturated or partially unsaturated monocyclic ring having 0-1 heteroatoms independently selected from O, N, and S.

2. The compound of claim 1, wherein $R^1$ is H.

3. The compound of claim 1, wherein $R^1$ is optionally substituted $C_{1-6}$ alkyl or $C_{3-7}$ cycloalkyl.

4. The compound of claim 1, wherein $R^1$ is H, ethyl, cyclopropyl or cyclopentyl.

5. The compound of claim 1, wherein $R^1$ is phenyl and one substituent at the para position of the phenyl is Q or -Z-Q.

6. The compound of claim 1, wherein $R^1$ is thiophen-2-yl, pyridin-3-yl, pyridin-4-yl, or 6-trifluoromethylpyridin-3-yl.

7. The compound of claim 1, wherein each of $R^2$ and $R^3$ is $C_{1-3}$ alkyl.

8. The compound of claim 1, wherein $R^4$ is $C_{1-6}$ aliphatic optionally substituted with 0-5 $J^4$.

9. The compound of claim 1, wherein $R^2$ is H and $R^3$ is $C_{1-3}$ alkyl.

10. The compound of claim 9, wherein $R^3$ is ethyl.

11. The compound of claim 8, wherein $R^4$ is $C_{3-10}$ cycloaliphatic optionally substituted with 0-5 $J^4$.

12. The compound of claim 11, wherein $R^4$ is cyclopentyl.

13. The compound of claim 1, wherein $R^8$ is H or —C(O)OR.

14. The compound of claim 13, wherein $R^8$ is H.

15. The compound of claim 13, wherein $R^8$ is —C(O)O$C_{1-6}$ alkyl.

16. The compound of claim 15, wherein $R^8$ is —C(O)OCH$_3$.

17. The compound of claim 1, wherein $R^1$ is optionally substituted 5-10 membered heteroaryl.

18. The compound of claim 17, wherein $R^1$ is optionally substituted with 0-3 —O-Q, halo, —C(O)N(R)-Q, or Q, in which each Q in Q, —C(O)N(R)-Q and —O-Q is independently optionally substituted with 0-5 $J^Q$.

19. The compound of claim 17, wherein the 5-10 membered heteroaryl represented by $R^1$ is substituted with —C(O)N(R)-Q and any remaining position with —O-Q, or Q, in which each Q in Q, —C(O)N(R)-Q and —O-Q is independently optionally substituted with 0-5 $J^Q$.

20. The compound of claim 19, wherein the Q in —C(O)N(R)-Q is H, $C_{1-4}$ aliphatic, $C_{1-4}$ haloaliphatic, $C_{3-7}$ cycloaliphatic, $C_{3-7}$ heterocycloaliphatic, or ($C_{1-6}$ alkoxy)$C_{1-6}$ alkyl.

21. The compound of claim 1, wherein each $R^1$ is optionally substituted $C_{6-10}$ aryl.

22. The compound of claim 21, wherein $R^1$ is optionally substituted with 0-3 —O-Q, halo, —C(O)N(R)-Q, or Q, in which each Q in Q, —C(O)N(R)-Q and —O-Q is independently optionally substituted with 0-5 $J^Q$.

23. The compound of claim 21, wherein the $C_{6-10}$ aryl represented by $R^1$ is phenyl optionally substituted at the para position with —C(O)N(R)-Q and any remaining position with —O-Q, halo, or Q, in which each Q in Q, —C(O)N(R)-Q and —O-Q is independently optionally substituted with 0-5 $J^Q$.

24. The compound of claim 23, wherein the Q in —C(O)N(R)-Q is H, $C_{1-4}$ aliphatic, $C_{1-4}$ haloaliphatic, $C_{3-7}$ cycloaliphatic, $C_{3-7}$ heterocycloaliphatic, or ($C_{1-6}$ alkoxy)$C_{1-6}$ alkyl.

25. The compound of claim 24, wherein Q of —C(O)N(R)-Q is methyl, ethyl, 1-methylpiperidin-4-yl, cyclopropyl, cyclopentyl, 3-furanyl, 3-fluoropyrrolidin-1-yl or 3,3-difluorocyclobutyl.

26. The compound of claim 24, wherein the phenyl is optionally substituted at any remaining position with halo, $C_{1-4}$ aliphatic, $C_{1-4}$ haloaliphatic, $C_{3-7}$ cycloaliphatic, $C_{3-7}$ heterocycloaliphatic, $C_{1-6}$ alkoxy, ($C_{1-6}$ alkoxy)$C_{1-6}$ alkyl or $C_{1-6}$ haloalkoxy.

27. A pharmaceutical composition comprising a compound of any one of claims 1, 13-5, 6-10, and 8-12, and a pharmaceutically acceptable carrier, adjuvant, or vehicle.

* * * * *

SEQUENCE LISTING

<160> NUMBER OF SEQ ID NOS: 3

<210> SEQ ID NO 1
<211> LENGTH: 19
<212> TYPE: PRT
<213> ORGANISM: Artificial
<220> FEATURE:
<223> OTHER INFORMATION: Plk 1

<400> SEQUENCE: 1

Lys Lys Lys Ile Ser Asp Glu Leu Met Asp Ala Thr Phe Ala Asp Gln
1               5                   10                  15

Glu Ala Lys